US008687862B2

(12) United States Patent
Hsu et al.

(10) Patent No.: US 8,687,862 B2
(45) Date of Patent: Apr. 1, 2014

(54) RETINAL IMAGE ANALYSIS SYSTEMS AND METHODS

(75) Inventors: Wynne Hsu, Singapore (SG); Mong Li Lee, Singapore (SG); Tien Yin Wong, Singapore (SG)

(73) Assignee: National University of Singapore, Crescent (SG)

( * ) Notice: Subject to any disclaimer, the term of this patent is extended or adjusted under 35 U.S.C. 154(b) by 552 days.

(21) Appl. No.: 12/936,702

(22) PCT Filed: Feb. 3, 2009

(86) PCT No.: PCT/SG2009/000040
§ 371 (c)(1),
(2), (4) Date: Oct. 7, 2010

(87) PCT Pub. No.: WO2009/126112
PCT Pub. Date: Oct. 15, 2009

(65) Prior Publication Data
US 2011/0026789 A1 Feb. 3, 2011

Related U.S. Application Data

(60) Provisional application No. 61/123,360, filed on Apr. 8, 2008.

(51) Int. Cl.
*G06K 9/00* (2006.01)

(52) U.S. Cl.
USPC .............................. 382/128; 341/79; 382/240

(58) Field of Classification Search
USPC ................ 382/100, 128–132, 173, 226, 240; 341/79

See application file for complete search history.

(56) References Cited

U.S. PATENT DOCUMENTS

| 4,109,237 | A | 8/1978 | Hill |
| 7,177,486 | B2 | 2/2007 | Stewart et al. |
| 7,646,903 | B2 * | 1/2010 | Kaftan et al. ................. 382/128 |
| 2008/0309881 | A1 | 12/2008 | Huang et al. |

FOREIGN PATENT DOCUMENTS

| JP | 05-123296 | 5/1993 |
| JP | 7210655 A1 | 8/1995 |
| JP | 10-243924 | 9/1998 |
| JP | 2002-542863 | 12/2002 |
| JP | 2005-508215 | 3/2005 |
| JP | 2006-204773 | 8/2006 |

(Continued)

OTHER PUBLICATIONS

Heneghan, Conor, et al. "Characterization of changes in blood vessel width and tortuosity in retinopathy of prematurity using image analysis." Medical Image Analysis 6.4 (2002): 407-429.*

(Continued)

*Primary Examiner* — Shefali Goradia
(74) *Attorney, Agent, or Firm* — Bracewell & Giuliani LLP

(57) ABSTRACT

A platform is proposed for automated analysis of retinal images, for obtaining from them information characterizing retinal blood vessels which may be useful in forming a diagnosis of a medical condition. A first aspect of the invention proposes that a plurality of characteristics of the retina are extracted, in order to provide data which is useful for enabling an evaluation of cardiovascular risk prediction, or even diagnosis of a cardiovascular condition. A second aspect uses fractal analysis of retinal images to provide vascular disease risk prediction, such as, but not limited to, diabetes and hypertension.

23 Claims, 25 Drawing Sheets

(56) References Cited

FOREIGN PATENT DOCUMENTS

| JP | 2007097740 A1 | 4/2007 |
|---|---|---|
| JP | WO2008010304 | 1/2008 |
| JP | 2008073188 A | 3/2008 |
| JP | 2008-513067 | 5/2008 |

OTHER PUBLICATIONS

Elena Martinez-Perez et al., "Retinal Vascular Tree Morphology: A Semi-Automatic Quantification," IEEE Transactions On Biomedical Engineering, IEEE Service Center, Piscataway, NJ, vol. 49, No. 8, Aug. 1, 2002, XP011070368, ISSN: 0018-9294.
Michael D. Knudtson et al., "Revised Formulas For Summarizing Retinal Vessel Diameters," Current Eye Research, IRL Press, Oxford, GB, vol. 27, No. 3, Jan. 1, 2003, pp. 143-149, XP009159238, ISSN:0271-3683, DOI: 10.1076/CEYR.27.3.143.16049.
H M Pakter et al., "Measuring Arteriolar-to-Venous Ratio In Retinal Photography Of Patients With Hypertension: Development And Application Of A New Semi-Automated Method," American Journal of Hypertension, Nature Publishing Group, US, vol. 18, No. 3, Mar. 1, 2005, pp. 417-421, XP025334904, ISSN: 0895-7061, DOI: 10.1016/J.Amjhyper.2004.10.011.
W E Hart et al., "Measurement And Classification Of Retinal Vascular Tortuosity," International Journal of Medical Informatics, Elsevier Scientific Publishers, Shannon, IR, vol. 53, No. 2-3, Feb. 1, 1990, pp. 239-252, XP004262424, ISSN: 1386-5056, DOI:10.1016/S1386-5056(98)00163-4.
N Patton et al., "Retinal Image Analysis: Concepts, Applications and Potential," Progress In Retinal And Eye Research, Oxford, GB, vol. 25, No. 1, Jan. 1, 2006, pp. 99-127, XP028074801, ISSN: 1350-9462, DOI: 10.1016/J.Preteyeres.2005.07.001.
Supplementary European Search Report, EP App. No. 09 72 9575, May 15, 2012, 10 Pages.
Stosic et al., "Multifractal Analysis of Human Retinal Vessels", 25(8) IEEE Trans. on Medical Imaging (Aug. 2006), pp. 1101-1107.
Yogesan et al., "Teleophtalmology", Springer 2008, ISBN 3540705155, 9783540705154, pp. 247-248.
International Search Report (PCT/SG2009/000040), dated Apr. 15, 2009.
Liew, Gerald, et al., The Retinal Vasculature as a Fractal: Methodology, Reliability, and Relationship to Blood Pressure, Available online Aug. 9, 2008, pp. 1951-1956, American Academy of Ophthalmology.
Cheung, Ning, et al., Quantitative Assessment of Early Diabetic Retinopathy Using Fractal Analysis, Diabetes Care, Jan. 2009, pp. 106-110, vol. 32, No. 1.
H. Narasimha-Iyer, et al., "Automatic Identification of Retinal Arteries and Veins From Dual-Wavelength Images Using Structural and Functional Features," IEEE Transactions of Biomedical Engineering, vol. 54, No. 8, Aug. 2007.
Office Action dated Jul. 6, 2013 for Related Application EP 09 729 575.2-1906.

* cited by examiner

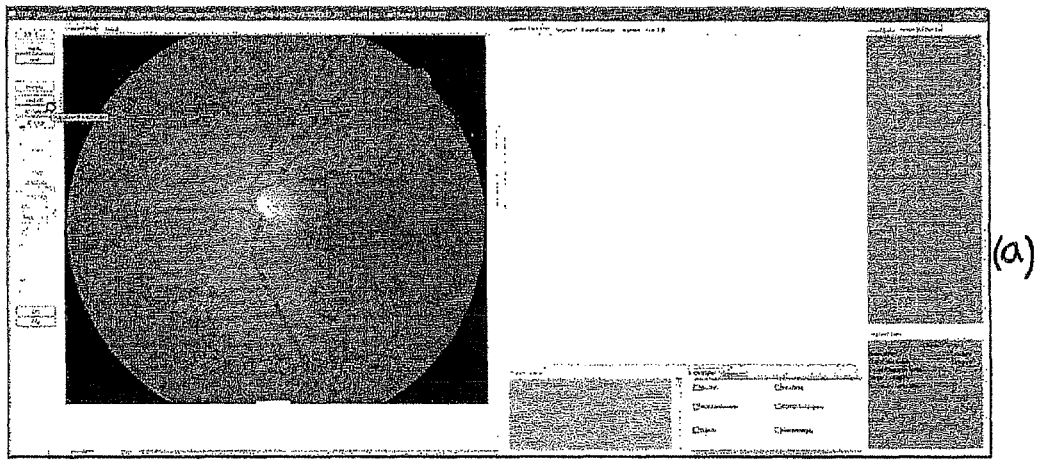
(a)
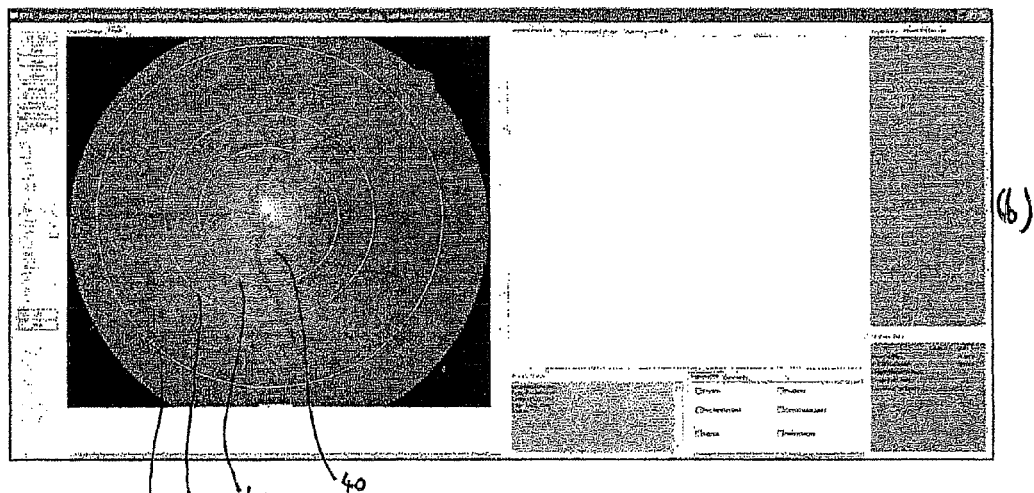
(b)
Fig. 4

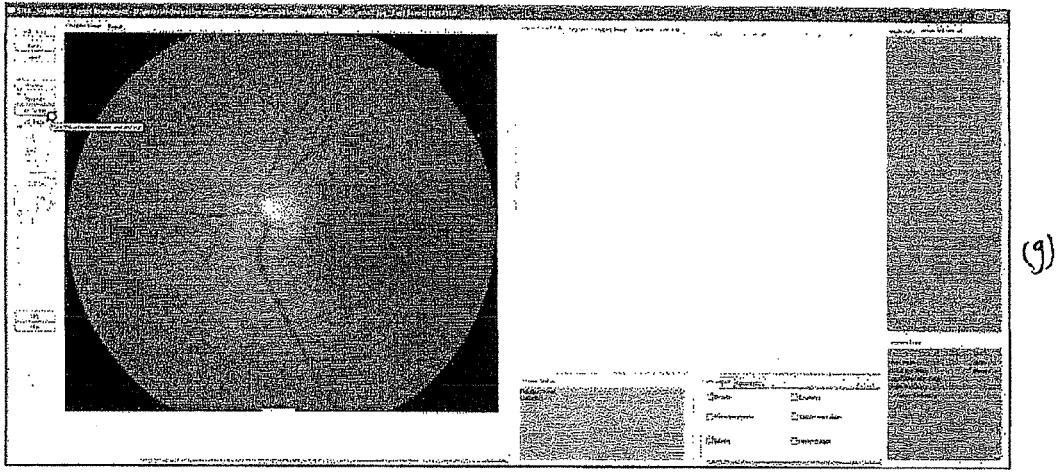
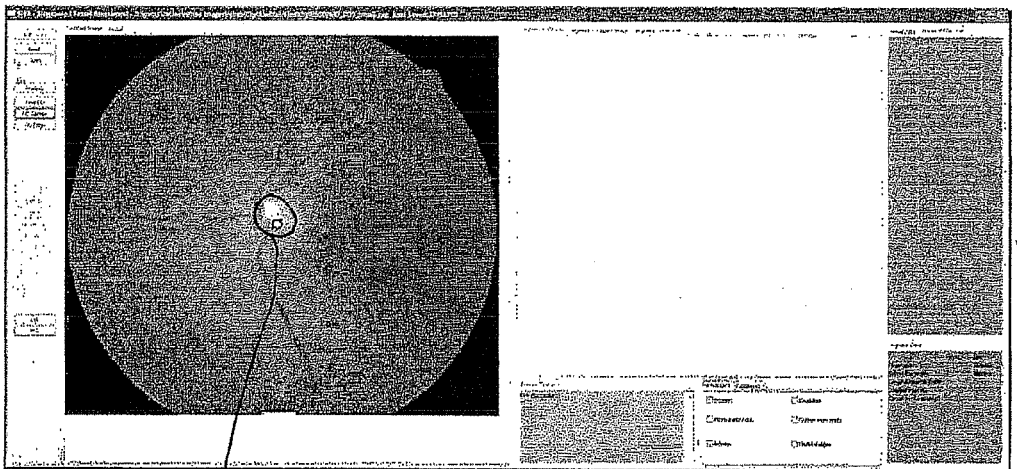
Fig. 4

| | Value | Units |
|---|---|---|
| Branching Coefficient | 1.24 | |
| Assymetry Factor | 0.35 | |
| Branching Angle | 76.59 | |
| Angles of Daughters | 74.30, 2.29 | |
| Angular Assymetry | 72.01 | |
| Junctional Exponent | 0.40 | |
| Zone C Data | | |
| Simple Tortuosity | 1.06 | |
| Curvature Tortuosity | 0.00000 | |
| LDRs | 0.00, 0.00 | |
| Mean width | 98.03 | Microns |
| STD of width | 6.62 | Microns |
| CRAE | 116.70 | Microns |
| CRVE | 207.61 | |
| AVR | 0.57 | |
| Zone B Data | | |
| Mean Width | 96.78 | Microns |
| STD of Width | 3.10 | Microns |
| CRAE | 116.77 | Microns |
| CRVE | 205.84 | |
| AVR | 0.57 | |

Fig. 8

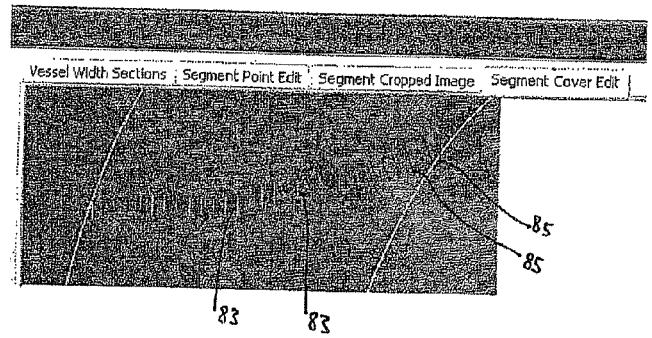
(a)
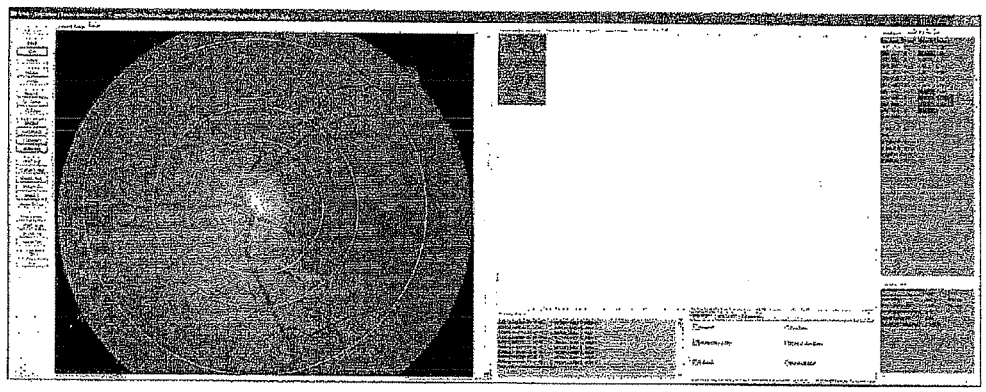
(b)
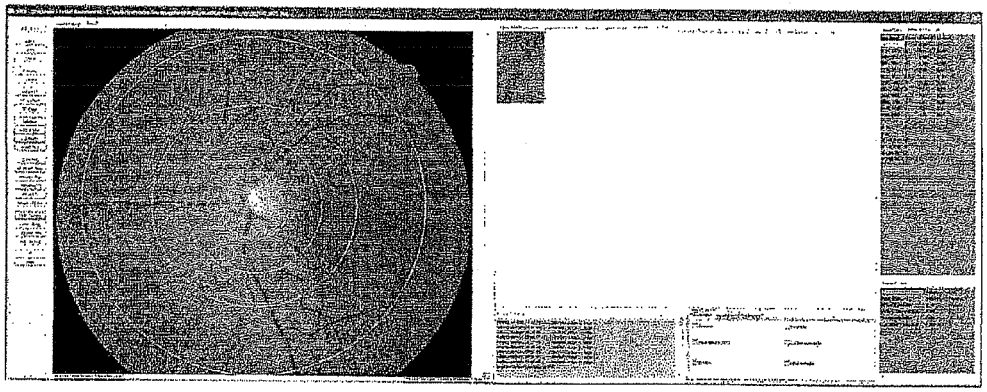
(c)
Fig. 11

Peripapillary atrophy

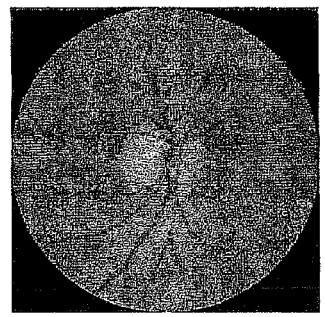 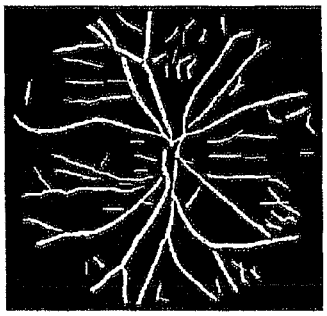 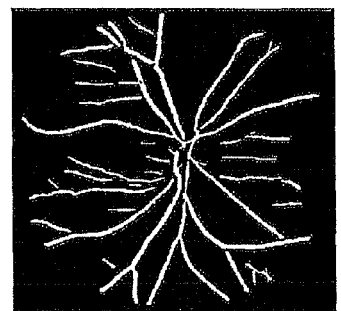
FIG 18                                                        800
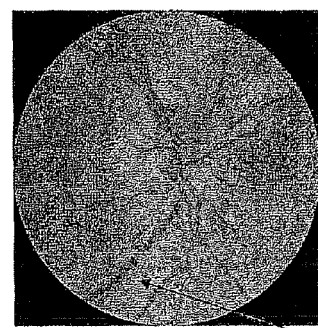 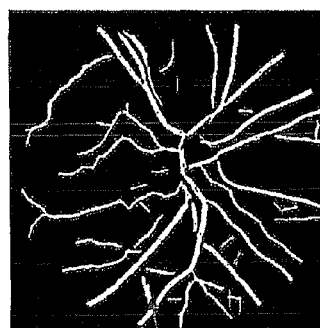 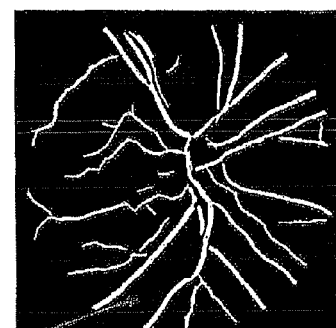
FIG 19                                                        900
Choroidal vessels removed
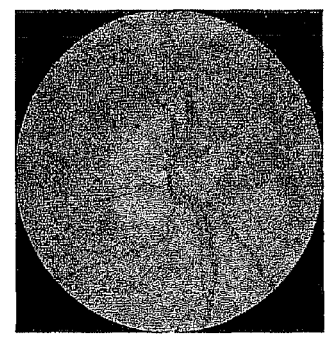 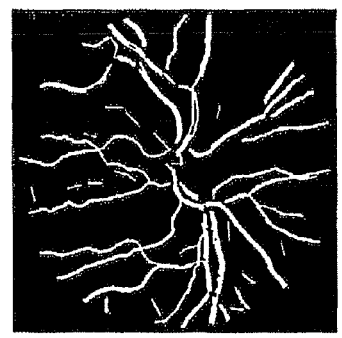 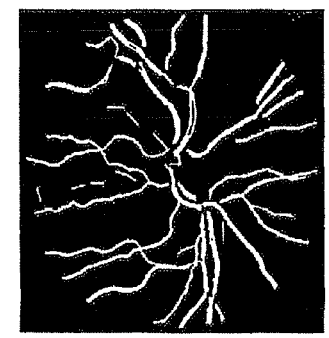
FIG 20                                                        1000

1100    1110

RETINAL IMAGE ANALYSIS SYSTEMS AND METHODS

RELATED APPLICATION

This application claims priority to PCT application PCT/SG2009/000040 filed Feb. 3, 2009, which claims priority to U.S. Provisional Patent Application No. 61/123,360, filed Apr. 8, 2008.

FIELD OF THE INVENTION

The present invention relate to systems and methods for analyzing retinal images, and for obtaining from them information characterizing retinal blood vessels which may be useful in forming a diagnosis of a medical condition.

BACKGROUND TO THE INVENTION

Existing non-invasive methods for monitoring cardiovascular disorders utilize blood pressure (see for example U.S. Pat. Nos. 5,961,467, 4,669,485, 5,365,924, 6,135,966, 5,634,467, 5,178,151). However, clinical studies have provided indications that changes in retinal vasculature (e.g., narrowing of retinal arterioles and widening of retinal venules) may be an early indicator of cardiovascular disease (CVD) and other conditions, such as hypertension and diabetes. The conditions of retinal arterioles and venules reflect the conditions of the blood vessels in the rest of the body. The ability to quantify the characteristics of retinal vessels is important to determine the severity of retinal arteriolar narrowing and other conditions.

Arterioles and venules are small branches of the main retinal arteries and veins respectively and their condition is indicative of the smaller blood vessels in the body. Measuring the diameter or widths of the arterioles and venules from detailed digital retinal images and calculating the arteriolar-to-venular diameter ratio (AVR) is one method of quantifying the imbalance between retinal arteriolar and venular calibre size. This measure can vary with different retinal vessels taken into calculation. More importantly, AVR provides information only on one aspect of retinal vascular change, namely retinal vessel calibre, and does not take into account the many structural alterations in the retinal vasculature. However, it is difficult to quantify the above characteristics of retinal vessels on a large scale as the process would involve repeated measurements of the diameters of the arterioles and venules in the retinal images by trained human graders. This is labour intensive and the results can vary when different human graders are used. For that reason, to our knowledge, no platform presently exists for non-invasive observation of cardiovascular orders using retinal image analysis.

It is also known that the branching patterns of retinal arterial and venous systems have fractal characteristics. A fractal is a geometrical pattern comprised of smaller parts or units which resemble the larger whole. Fractals have been used to characterise diverse natural shapes such as the branching patterns of trees, the shapes of coastlines, the pattern of electrocardiograph tracings as well as retinal microcirculation. The fractal (or fractional) dimension (D) is one measure associated with fractals and has a range of definitions. However, it can be considered as a statistical quantity that provides an indication of how completely a fractal appears to fill the space occupied by the fractal as finer and finer scales are zoomed in upon. In other words, the fractal dimension can be considered as the number of smaller units comprising the larger unit that fit into that larger unit. The fractal dimension is always smaller than the number of dimensions in which the fractal being considered exists.

It was suggested in Patton N, Aslam T, MacGillivray T, Pattie A, Deary I J, Dhillon B., Retinal vascular image analysis as a potential screening tool for cerebrovascular disease: a rationale based on homology between cerebral and retinal microvasculatures. *J. Anat.* 2005; 206:319-348, that fractals offer a natural, global, comprehensive description of the retinal vascular tree because they take into account both the changes in retinal vessel calibre and changes in branching patterns.

In Mainster M. A., The fractal properties of retinal vessels: embryological and clinical implications, *Eye*, 1990, 4 (Pt 1):235-241, the analysis of digitised fluorescein angiogram collages revealed that retinal arterial and venous patterns have fractal dimensions of $1.63\pm0.05$ and $1.71\pm0.07$ respectively, which is consistent with the $1.68\pm0.05$ dimension known from diffusion limited aggregation.

In Daxer A, The fractal geometry of proliferative diabetic retinopathy: implications for the diagnosis and the process of retinal vasculogenesis. *Curr Eye Res.* 1993; 12:1103-1109, retinal vessel patterns with neovascularisation at or near the optic disc (NVD) were compared with the vascular patterns of normal eyes. The presence of NVD in an eye is a high risk characteristic for severe visual loss requiring laser treatment. Fractal dimensions were calculated from digitised photographs using a density-density correlation function method. The mean fractal dimension D for vessel patterns with NVD was significantly higher ($D=1.845\pm0.056$) compared with the control group ($D=1.708\pm0.073$). A cut-off value for the fractal dimension is suggested to be 1.8, with higher values being potentially indicative of proliferative changes.

Hence, fractal geometry provides a global and more accurate description of the anatomy of the eye than classical geometry. Fractal patterns characterise how vascular patterns span the retina and can therefore provide information about the relationship between vascular patterns and retinal disease.

SUMMARY OF THE INVENTION

The present invention aims to provide a platform for automated analysis of a retinal image, including automatically tracing one or more paths of one or more vessels of a retinal image, and for obtaining from them information characterizing retinal blood vessels which may be useful in forming a diagnosis of a medical condition.

A first aspect of the invention proposes in general terms an automated retinal image analysis system and/or method that permit a plurality of characteristics of the retina to be extracted, in order to provide data which is useful for enabling an evaluation of cardiovascular risk prediction, or even diagnosis of a cardiovascular condition. Preferred embodiments of the invention permit large scale grading of retina images for cardiovascular risk prediction with high intra-grader and inter-grader reliability.

In one expression, the first aspect of the invention proposes a retinal image analysis method including:

(i) automatically tracing one or more paths of one or more vessels of a retinal image;

(ii) automatically generating a trace image comprising the one or more traced paths;

(iii) automatically identifying a plurality of vessel segments which are portions of said vessels;

(iv) using the vessel segments to calculate automatically a plurality of parameters; and (v) outputting the plurality of parameters.

In another expression, the first aspect of the invention proposes retinal image analysis system comprising:

a processor for:

(i) automatically tracing one or more paths of one or more vessels of a retinal image;

(ii) automatically generating a trace image comprising the one or more traced paths;

(iii) automatically identifying a plurality of vessel segments which are portions of said vessels;

(iv) using the vessel segments to calculate automatically a plurality of parameters; and (v) outputting the plurality of parameters.

In another expression, the first aspect of the invention proposes retinal image analysis system comprising:

(i) computer readable program code components configured for automatically tracing one or more paths of one or more vessels of a retinal image;

(ii) computer readable program code components configured for automatically generating a trace image comprising the one or more traced paths;

(iii) computer readable program code components configured for automatically identifying a plurality of vessel segments which are portions of said vessels;

(iv) computer readable program code components configured for using the vessel segments to calculate automatically a plurality of parameters; and (v) computer readable program code components configured for outputting the plurality of parameters.

A second aspect of the invention proposes in general terms an automated retinal image analysis system and/or method that use fractal analysis of retinal images to provide disease risk prediction, such as, but not limited to, diabetes and hypertension.

In one expression, the second aspect of the invention provides a retinal image analysis method including:

automatically tracing one or more paths of one or more vessels of a retinal image;

automatically generating a trace image comprising one or more traced paths;

automatically calculating a fractal capacity dimension of the trace image;

comparing the calculated fractal capacity dimension with a benchmark fractal capacity dimension; and generating an estimate for future risk of disease (such as cardiovascular disease) on the basis of the comparison.

The method may include refining the trace image to remove errors in the trace image and calculating a refined fractal capacity dimension of the refined trace image.

Preferably, the fractal capacity dimension is a multifractal capacity dimension, which is superior to a mono-fractal capacity dimension.

Preferably, the method includes setting a radius of the optic disc of the retinal image prior to automatically tracing the retinal image.

Preferably, prior to automatically tracing the retinal image, the method includes cropping or scaling the retinal image to minimise deleterious aspects of the retinal image and enable retinal image comparisons.

Suitably, the method includes repeating refining of the trace image if errors in the trace image remain after previous refining.

Suitably, the method includes interrogating a data store and selecting diagnostic data based on the calculated refined fractal capacity dimension.

Suitably, the method includes automatically generating a report including the retrieved diagnostic data.

In another expression, the second aspect of the invention provides a retinal image analysis system comprising:

a processor for:

automatically tracing one or more paths of one or more vessels of a retinal image;

automatically generating a trace image comprising one or more traced paths;

automatically calculating a fractal capacity dimension of the trace image;

comparing the calculated fractal capacity dimension with a benchmark fractal capacity dimension; and generating an estimate for future risk of disease on the basis of the comparison.

Preferably, the system further comprises an output device coupled to be in communication with the processor for displaying the trace image and a refined trace image.

Preferably, the system further comprises a data store coupled to be in communication with the processor for storing diagnostic data.

Suitably, the processor interrogates the data store and selects diagnostic data based on the calculated fractal capacity dimension.

Suitably, the processor automatically generates a report including the retrieved diagnostic data.

In a further expression, the second aspect of the invention provides a retinal image analysis system comprising:

computer readable program code components configured for automatically tracing one or more paths of one or more vessels of a retinal image;

computer readable program code components configured for automatically generating a trace image comprising one or more traced paths;

computer readable program code components configured for automatically calculating a fractal capacity dimension of the trace image;

computer readable program code components configured for comparing the calculated fractal capacity dimension with a benchmark fractal capacity dimension; and computer readable program code components configured for generating an estimate for future risk of disease on the basis of the comparison.

BRIEF DESCRIPTION OF THE DRAWINGS

By way of example only, preferred embodiments of the invention will be described more fully hereinafter with reference to the accompanying drawings, wherein:

FIG. 8 is a screenshot showing information generated by the method of FIG. 2 pertaining to a vessel, as well as summary attributes such as the CRAE and CRVE measures for the respective zones;

FIG. 11 is composed of FIGS. 11(a), 11(b) and 11(c), which are screenshots showing the effect of optimization in the method of FIG. 2 to automatically cover bad segment widths according to embodiments of the present invention;

FIG. 18 is a series of screenshots showing the removal of short lines from the trace image which do not correspond to vessels during refining of the trace image according to embodiments of the second aspect of the present invention;

FIG. 19 is a series of screenshots showing the removal of choroidal vessels from the trace image during refining of the trace image according to embodiments of the second aspect of the present invention;

FIG. 20 is a series of screenshots showing the removal of artefacts from the trace image during refining of the trace image according to embodiments of the second aspect of the present invention;

DETAILED DESCRIPTION OF THE EMBODIMENTS

Figure 1:
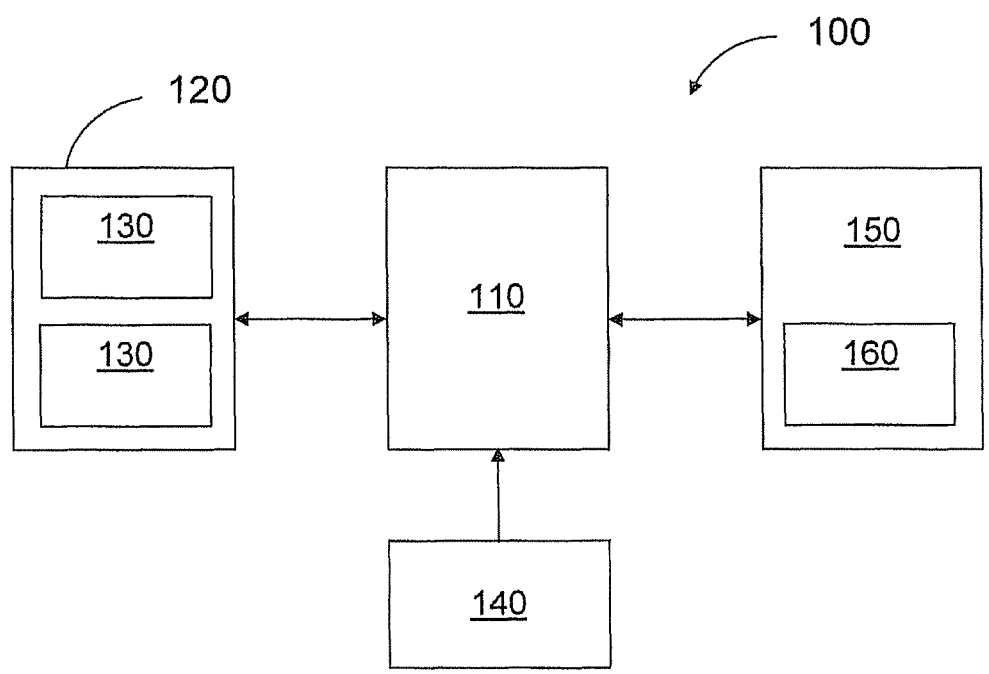
FIG. 1 is a schematic diagram of a diagnostic retinal image system according to embodiments of the present invention.

Referring to FIG. 1, there is provided a diagnostic retinal image system 100 in accordance with embodiments of the present invention. The system 100 comprises a processor 110 coupled to be in communication with an output device 120 in the form of a pair of displays 130 according to preferred embodiments of the present invention. The system 100 comprises one or more input devices 140, such as a mouse and/or a keyboard and/or a pointer, coupled to be in communication with the processor 110. In some embodiments, one or more of the displays 130 can be in the form of a touch sensitive screen, which can both display data and receive inputs from a user, for example, via the pointer.

The system 100 also comprises a data store 150 coupled to be in communication with the processor 110. The data store 150 can be any suitable known memory with sufficient capacity for storing configured computer readable program code components 160, some or all of which are required to execute the present invention as described in further detail hereinafter.

According to one embodiment, the processor 110 is in the form of a Pentium® D, CPU 2.80 GHz and the data store 150 comprises 1 GB of RAM and 232 GB local hard disk space. The pair of displays 130 are in the form of two 21-inch monitors allowing image displays at 1280×1024 resolution. NVIDIA Quadro FX 1400 graphics cards are also employed. The skilled addressee will appreciate that the present invention is not limited to this particular implementation.

The data store 150 stores configured computer readable program code components 160, some or all of which are retrieved and executed by the processor 110. Embodiments of the present invention reside in a diagnostic retinal image system 100 comprising computer readable program code components configured for automatically tracing one or more paths of one or more vessels of a retinal image. The system 100 also comprises computer readable program code components for generating a trace image comprising one or more traced paths. The system further comprises computer readable program code components configured for refining the trace image to remove errors in the trace image.

As described in the following, the system 100 typically includes program code components for automatically identifying an optic disc. Cropping of a consistently defined area relative to optic disc size allows comparison of different images from the same individual taken at different times and permits comparison of images from dissimilar individuals because the defined area relative to optic disc size of the same image is not influenced by image magnification and different angles of photography. The system 100 further comprises a comprehensive reporting facility which automatically generates a report usable by both clinicians and patients and reduces the level of human intervention enabling the efficiency of grading retinal images and reporting to be improved. Embodiments of the present invention allow multiple retinal images of a patient to be linked on a single report.

The retinal image system is configured to operate in accordance with either of the aspects of the invention, as described below, thereby performing the series of steps shown in either of FIGS. 2 and 12 respectively.

1. First Aspect of the Invention

Figure 2:
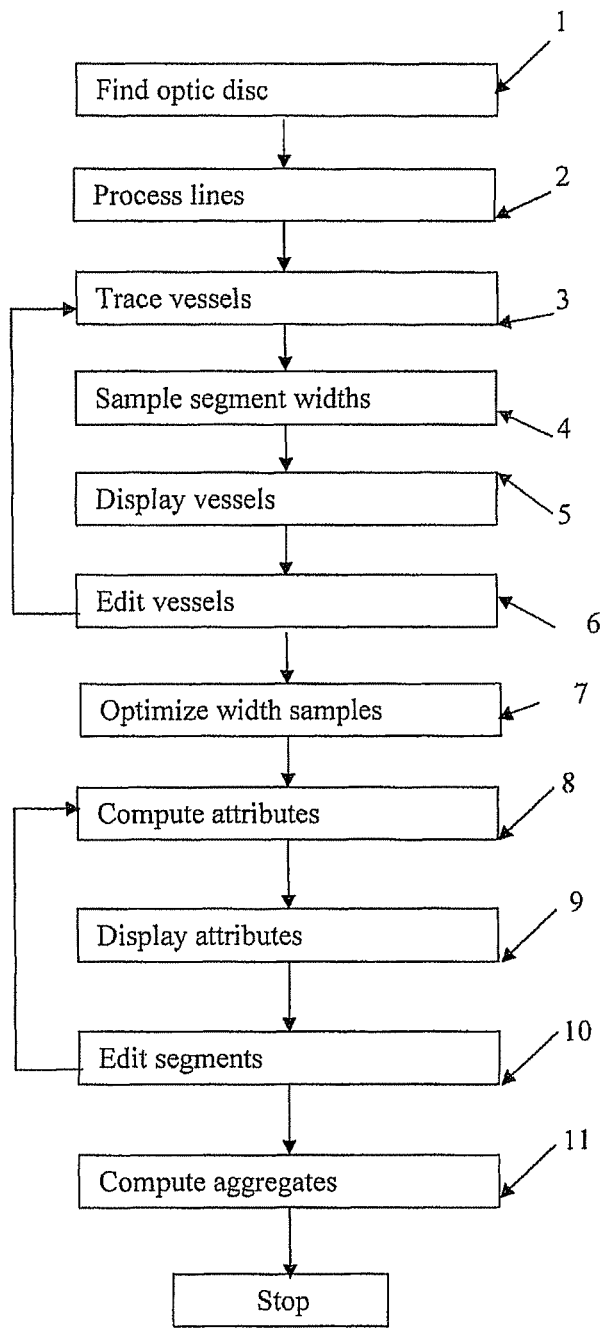
FIG. 2 is a flow diagram of method which is an embodiment of the first aspect of the invention.
Figure 3:
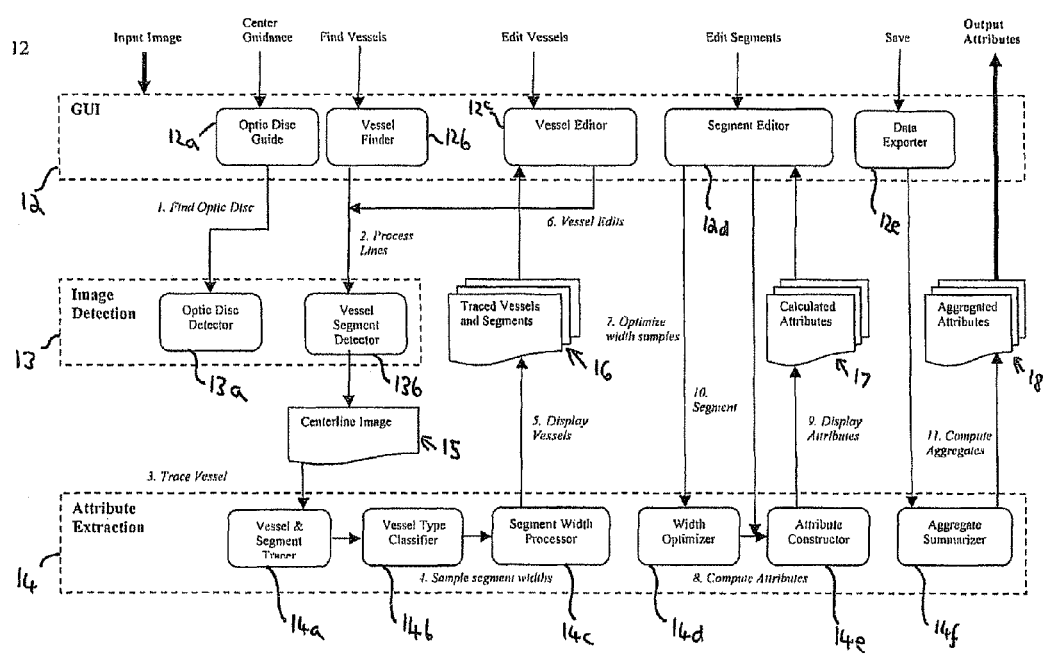
FIG. 3 illustrates the structure and operation of a computer program for carrying out the method of FIG. 2.

Turning to FIG. 2, the steps of a method which is a first embodiment of the invention are illustrated. The structure of the computer program (e.g. as implemented by the system 100 of FIG. 1) for carrying out the method is illustrated in FIG. 3, in which the steps labelled 1-11 correspond to those of FIG. 2. The program comprises a GUI (graphical user interface) module 12, an image detection module 13, and an attribute extraction module 14.

The input to the method of FIG. 2 is a disc-centred retinal photograph, for example of the kind which can be produced by a Zeiss FF3 fundus camera, which has been digitized.

1.1 Optic Disc Detection (Step 1)

In a first step of the method of FIG. 2, the region of the photograph corresponding to the optic disc is detected for reliable grading of the retina image. We here discuss three modes for the optic disc detection, any one of which can be used. The process is performed by the unit 12a of the GUI 12 and the optic disc detector 13a of the Image detection module 13, with the proportion of the work performed by each of the units 12a, 13a depending upon which of the modes is used.

The first mode is a fully automatic detection that is based on wavelet processing and ellipse fitting. The system employs a Daubechies wavelet transform to approximate the optic disc region. Next, an abstract representation of the optic disc is obtained using an intensity-based template. This yields robust results in cases where the optic disc intensity is highly non-homogenous. An ellipse fitting algorithm is then utilized to detect the optic disc contour from this abstract representation (see P. M. D. S Pallawala, Wynne Hsu, Mong Li Lee, Kah-Guan Au Eong. Automated Optic Disc Localization and Contour Detection Using Ellipse Fitting and Wavelet Transform, in 8th European Conference on Computer Vision (ECCV), Prague, Czech Republic, May 2004).

The second mode is a semi-automatic detection where the user positions a circle to approximate the cup area. Optic disc detection using the method described above is then carried out beyond the user-specified cup area.

The third mode of optic disc detection is primarily manual which requires the user to pinpoint the centre and the edge of the optic disc, following which an outline of the optic disc is traced on the retina image. This can be done using the optic disc guide portion 12a of the GUI 12.

Figure 4:
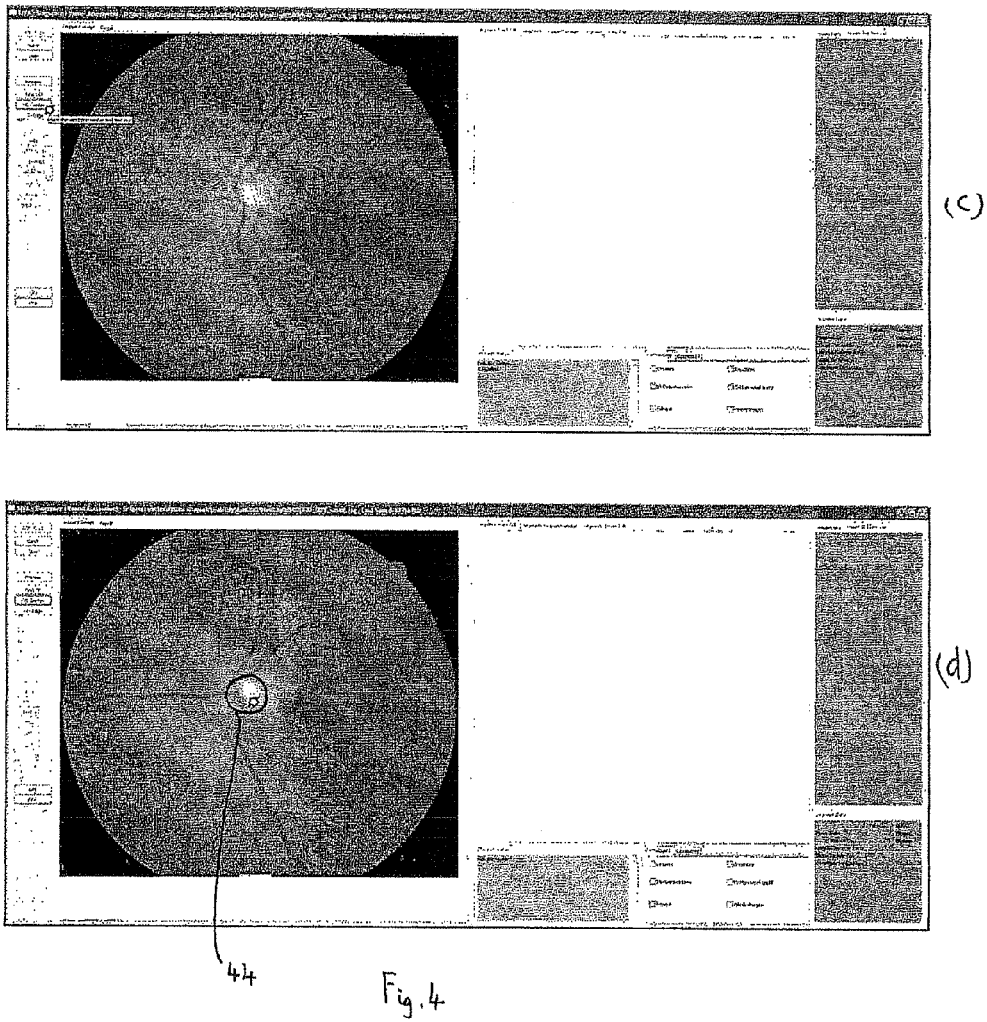
FIG. 4, which is composed of FIGS. 4(a) to 4(k), is a series of screenshots showing the three modes of optic disc detection in the method of FIG. 2.
Figure 4:
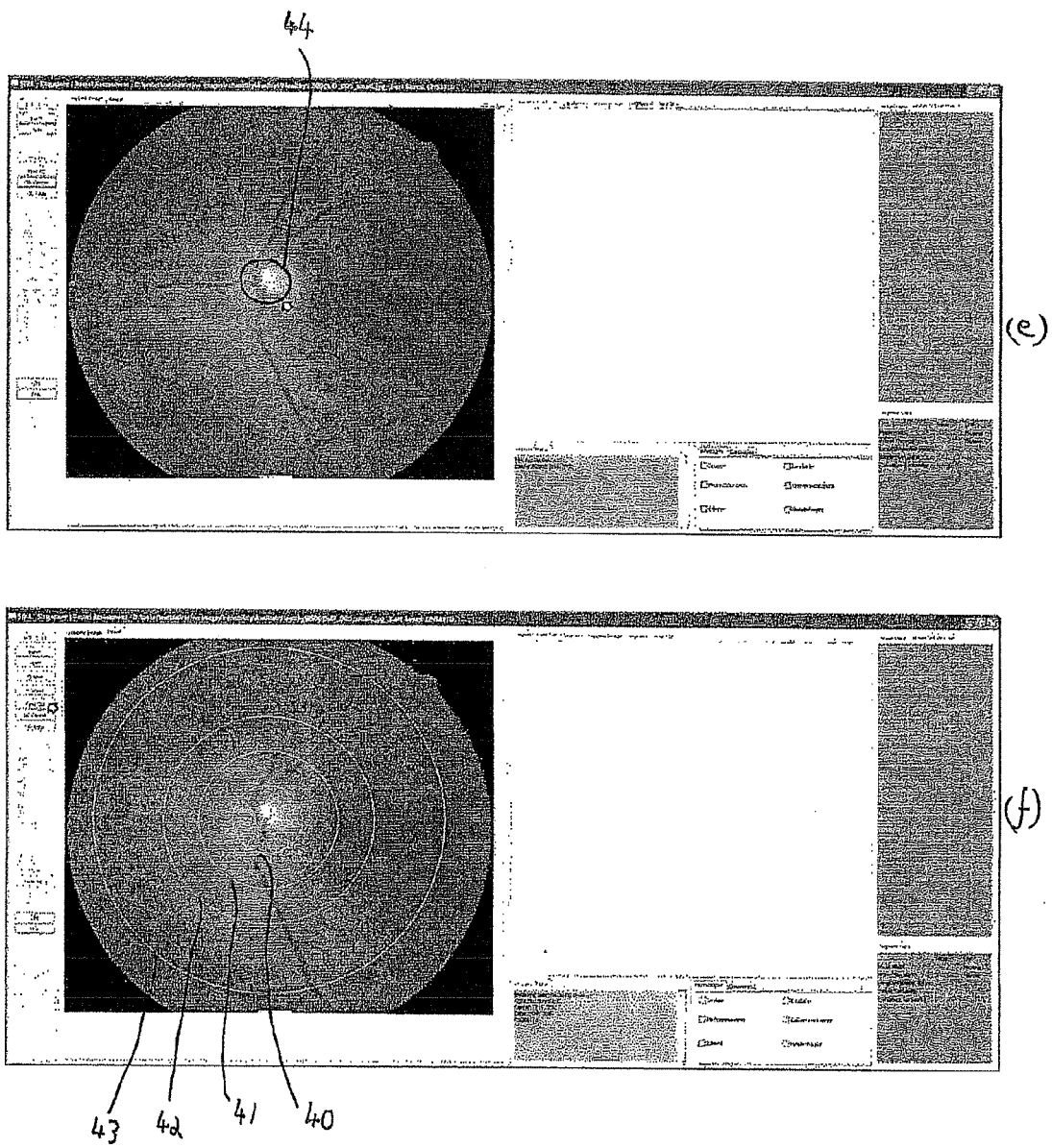
Figure 4:
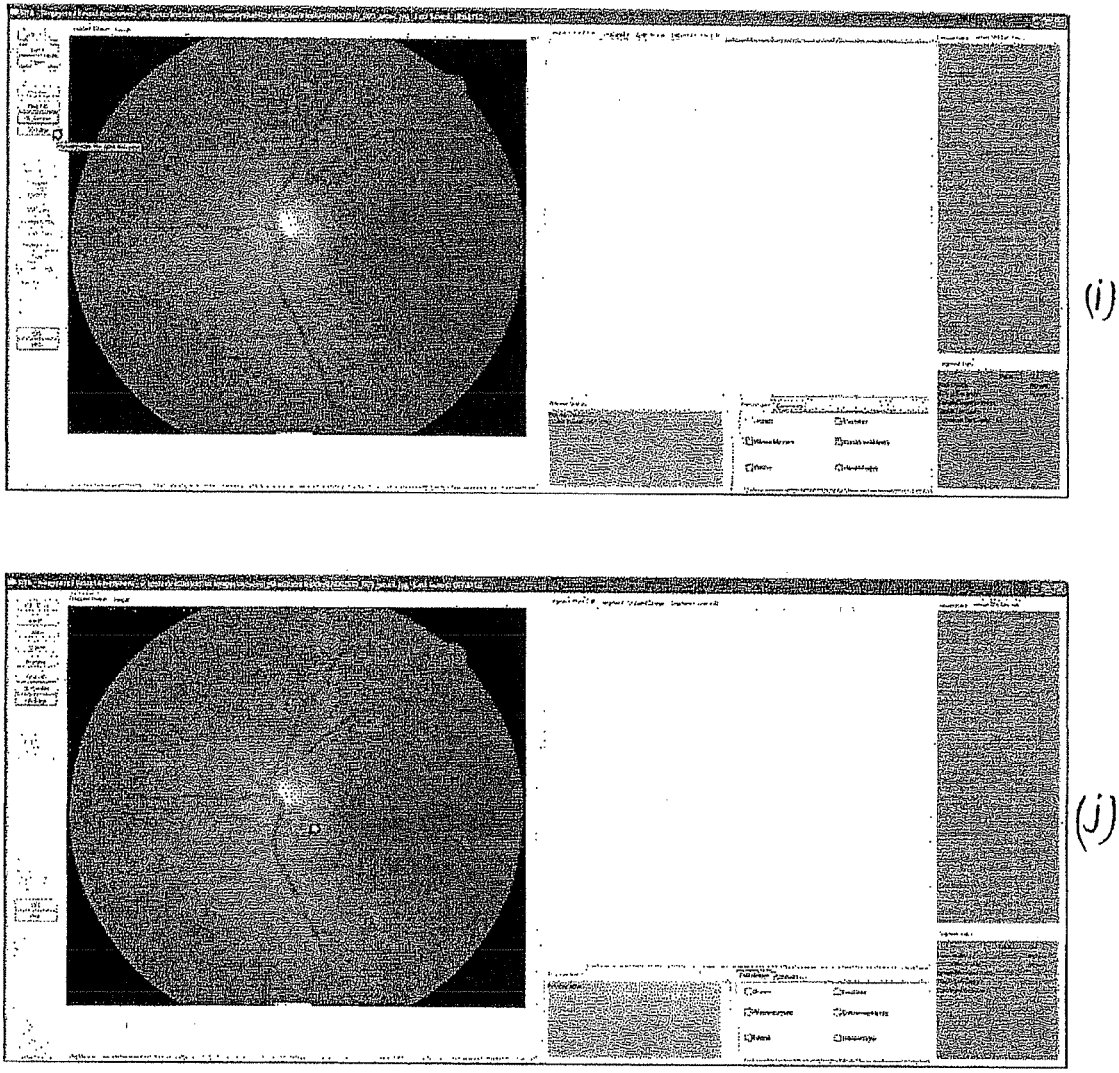
Figure 4:
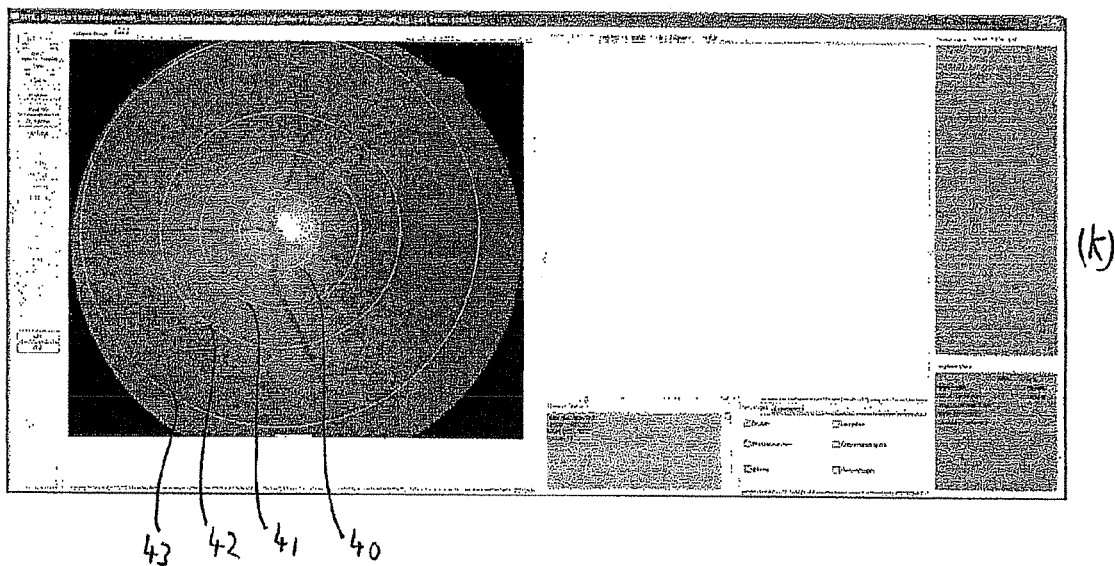

FIG. 4 is a series of screenshots showing what the GUI displays during the three modes of optic disc detection.

FIGS. 4(a) and 4(b) show the fully-automated mode. The user is initially presented with screen FIG. 4(a), and upon a command, the unit 13a, generates the screen FIG. 4(b). The optic disc is detected as the circular area 40 with radius r. Based on the optic disc radius r, the unit 13a defines three zones A, B, C from the centre of the optic disc as follows: Zone A is the area within a circle 41 with radius 2r; Zone B is a concentric area formed by subtracting Zone A from a circle 42 with radius 3r; Zone C is a concentric area formed by subtracting Zone A from a circle 43 with radius 5r, and thus overlaps with zone B.

FIGS. 4(c) to 4(f) show the sequence of steps in the semi-automated mode. FIG. 4(c) is equivalent to FIG. 4(a). FIG. 4(d) shows how the user manually positions a circle 44 near the optic disc centre. FIG. 4(e) shows how the user resizes the circle 44 by dragging a mouse. After doing so, and thereby covering the optic disc cup with the resized circle, he clicks on "Find OD" on the GUI 12, and the system generates circles 40, 41, 42, 43, shown in FIG. 4(f), having the meaning above.

FIGS. 4(g) to 4(k) show the manual mode. FIG. 4(g) is again equivalent to FIG. 4(a). FIG. 4(h) shows how a user uses a mouse to place a circle 44 at the optic disc centre (resizing is not done yet) and then clicks. FIG. 4(i) shows how the user then indicates the command "OD edge". FIG. 4(j) shows how the user then clicks on an edge point of the optic disk he wishes to draw. FIG. 4(k) shows what the screen then shows: the circles 40, 41, 42, 43 generated from the selected optic disc centre and the selected edge point.

1.2 Vascular Structure Extraction and Tracing

The algorithm for vascular structure extraction is performed by the unit 13b as controlled by a vessel finder unit 12b of the GUI 12, and is based on the work in S. Garg, J. Sivaswamy, S. Chandra. Unsupervised Curvature-Based Retinal Vessel Segmentation, Technical Report, Institute of Information Technology, Hyderabad, India, 2007. The retinal vessels are modelled as trenches and the centre lines of the trenches are extracted using curvature information (step 2 of FIG. 2). The result is an image (labelled 15 on FIG. 3) in which each of the trenches is indicated by a centreline.

The complete vascular structure is then extracted (step 3 of FIG. 2) by an attribute extraction module 14 using a modified region growing method. Seed points are placed at the start of Zone B to initiate the tracing of vessel segments. The vessels are traced by the unit 14a in a depth first manner whenever a branch point or cross-over is encountered. The widths samples of each vessel segment are automatically determined at fixed intervals. This is done by a unit 14c.

1.3 Classification of Retinal Arterioles and Venules (Step 4)

The unit 14b of the attribute extraction module 14 identifies arteries and veins as follows (the terms "vein" and "venule" are used interchangably in this document, as are the terms "arteries" and "artioles"). First, we select the first 15 diameter lines for each vessel. This is to minimize the effect of local variation in intensity. Then, for each selected diameter line, we obtain its intensity profile in the form of a histogram. From the histogram, we select the top five most frequently occurring values and calculate the mean value.

Next, we apply the k-means algorithm to cluster these mean values of all the vessels into two classes, vein and artery. The k-means algorithm initially picks two values as seeds. It then iteratively computes the distances from each point to the two centers. Points are re-assigned to the cluster of the nearest center. After several iterations, the clusters will converge.

After obtaining the two cluster centers, we label the 15 diameter lines as either veins or arteries depending of its distance to the two centers. We count the number of diameter lines that have been labeled as veins and arteries respectively. A majority voting system is used to finally classify the given vessel as either vein or artery.

Figure 6:
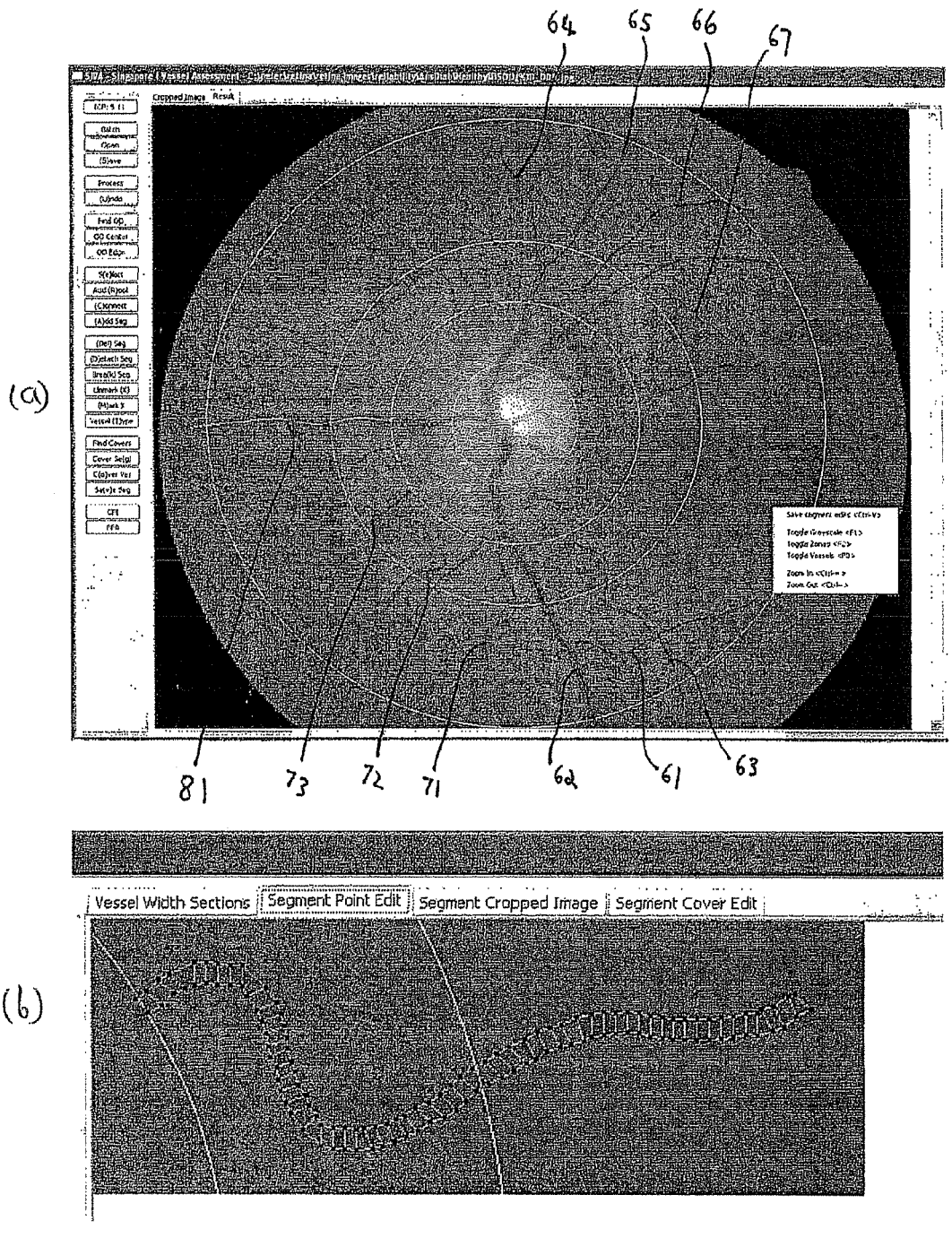
FIG. 6 is composed of FIGS. 6(a) and 6(b), which respectively show a trace image in which retinal paths have been assigned, and an expanded portion of the trace image used to edit the highlighted vessel segment in the method of FIG. 2.

In step 5 the result is displayed by the GUI, as shown in FIG. 6 (this is the image shown as 16 in FIG. 3). FIG. 6(a) shows the overall retinal image with lines indicating vessel segments. Some of the venules are labelled by reference numerals 61, 62, 63, 64, 65, 66, 67. Some of the arterioles are labelled 71, 72, 73. The arteriole 81 is shown brighter because it has been selected by a user. FIG. 6(b) shows how the user may display a larger version of a vessel segment, and that if so the width at each point along the vessel segment is displayed by a line orthogonal to the length direction of the vessel segment 44. The system attempts to sample the widths at equal intervals. Several operations are provided for the user to refine vascular structure that has been extracted and tracked. The user may edit the data (step 6) using a vessel editor unit 12c of the GUI 12, which is shown in FIG. 3 as receiving user input ("edit vessels"). This may include any one of more of adding missed vessel segments, deleting dangling vessel segments, breaking vessel segments, marking and unmarking crossover vessel segments, and changing vessel type.

Figure 7:
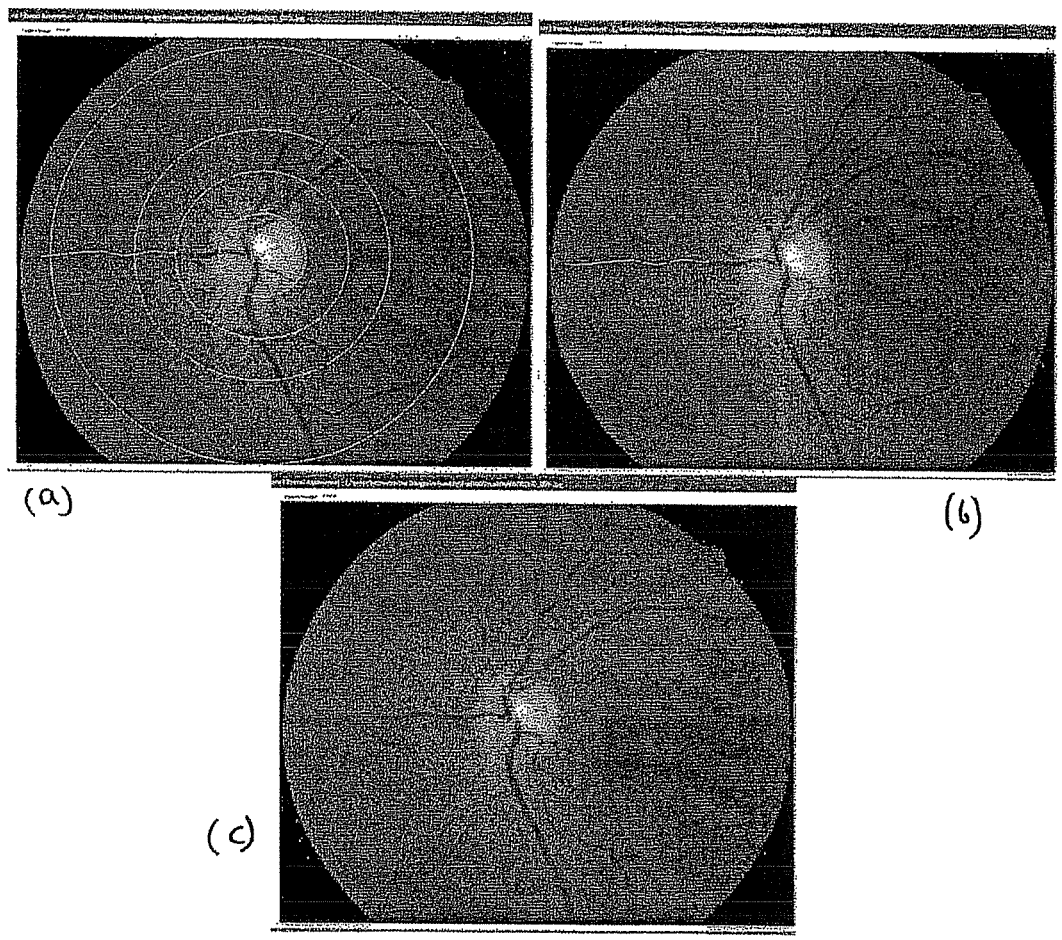
FIG. 7 is composed of FIGS. 7(a), 7(b) and 7(c), which are screenshots showing the toggling capabilities that allow the user to remove visual obstructions when inspecting the image and editing the centerlines that make up the tree structures of the vessel in the method of FIG. 2.

The result, is passed back to the vessel segment detector 13b. The method loops back to step 3 (optionally many times) until the user is satisfied. Some of the various views shown to the user by the GUI at this time are shown in FIG. 7. The user can toggle between these views.

1.4 Computation of Measurements (Step 8)

The unit 14d optimises the width samples by discarding bad samples based on a special heuristic to improve standard deviation (step 7). This heuristic comes in the form of maximising an objective function that balances between standard deviation (lower is better) of the widths and the number of samples retained (higher is better). A standard optimisation technique is used to retain the widths that maximise the objective function. FIG. 11 illustrates is the effect of applying the width optimiser.

In FIG. 11a the bright lines (such as lines 83) along the segment are the sample widths retained and the dark lines (such as lines 85) are the sample widths discarded by the width optimiser. Notice that the discarded sample widths are inaccurate representations of the width of the segment. The width optimiser is applied to all segments. FIG. 11B shows a screen shot before this process with FIG. 9 (an enlargement of the right of FIG. 11B), indicating vessels that have wide variations in sampled widths using dark boxes. FIG. 11C shows a screen shot after this process is applied with the right of the figure containing no dark boxes. This indicates that the current variation of sampled widths is not overly wide.

The unit 14e then computes the attributes of the segments identified and edited. Note that a vessel is a binary tree with the property that each node has exactly zero or two child nodes. Each node in the vessel binary tree denotes a segment. A segment is a list of points on a line that does not include any branching points. The segment at the root node of a vessel is called the root segment and the first point in the segment at the root node is the root point. A segment could branch out into two daughter segments.

1.4.1 Segment Measurements

Let s be a segment, the following measurements are defined as functions of s.

Mean Width $\omega(s)$: Sample widths of s are taken at fixed intervals. The mean width of s is a simple average of the sample widths. $\omega_B(s)$ and $\omega_C(s)$ denote averages of sample widths within zones B and C respectively.

Standard Deviation $\sigma(s)$: Sample widths of s are taken at fixed intervals. The standard deviation of width of s is calculated from those samples. $\sigma_B(s)$ and $\sigma_C(s)$ denote the standard deviations of samples within Zone B and C respectively.

Length $\lambda(s)$: The length of s is computed as the sum of the pairwise Euclidean distance between two adjacent points in s, that is, it is the arc of the segment. $\lambda_B(s)$ and $\lambda_C(s)$ denote the lengths within zones B and C respectively.

Simple Tortuosity $\tau(s)$: Simple tortuosity is calculated as the arc-chord ratio, $\tau(s)=\lambda(s)/C(s)$ where C is the chord of s, that is, the Euclidean distance between the first and last point in s. Similarly, $\tau_B(s)=\lambda_B(s)/C_B(s)$ and $\tau_B(s)=\lambda_C(s)/C_C(s)$ for Zone B and C respectively, where the chord within Zones B and C is measured using the first and last point in s within them.

Curvature Tortuosity $\zeta(s)$: This is computed from formula T4 given in W. E. Hart, M. Goldbaum, B. Cote, P. Kube, M. R. Nelson. Automated measurement of retinal vascular tortuosity, Proceedings AMIA Fall Conference, 1997. Since the points in the segment are discrete, the integral is estimated using summation to give, $$\varsigma(s) = \frac{\sum_{i=1}^{|s|} \frac{[x'(t_i)y''(t_i) - x''(t_i)y'(t_i)]^2}{[y'(t_i)^2 + x'(t_i)^2]^3}}{\lambda(s)}$$

where $t_i$ is the i-th point in s and $|s|$ is the number of points in s. The first order parametric differentials are estimated using $f'(t_i)=f(t_{i+1})-f(t_{i-1})$ and the second order is estimated using $f''(t_i)=f'(t_{i+1})-f'(t_{i-1})$ where f is the parametric function x or y. For tortuosity within Zone C, we have $$\varsigma_C(s) = \frac{\sum_{i=1}^{|s|} \frac{[x'(t_i)y''(t_i) - x''(t_i)y'(t_i)]^2}{[y'(t_i)^2 + x'(t_i)^2]^3}}{\lambda_C(s)}$$

where $|s_C|$ is the last segment point within Zone C.

1.4.2 Zone B Vessel Measurements

All Zone B measurements considers only the root segment within Zone B, that is, if the root segment extends outside of Zone B, only the part of the segment within Zone B will be computed. Let v be a vessel, the following Zone B measures are provided:

Mean Width $\omega_B(v)$: The mean width of a vessel v, in Zone B, is the mean width of the root segment.

Standard Deviation $\sigma_B(v)$: The standard deviation of a vessel v in Zone B is the standard deviation of the root segment.

$CRVE_B$: The widths of the six largest venules are combined using the formula given in M. D. Knudtson, K. E. Lee, L. D. Hubbard, T. Y. Wong, R. Klein, B. E. Klein. Revised formulas for summarizing retinal vessel diameters. Curr Eye Res., 2003; 27: 143-149. This gives a single value for the whole of zone B.

$CRAE_B$: The widths of the six largest arterioles are combined using the formula given in M. D. Knudtson, K. E. Lee, L. D. Hubbard, T. Y. Wong, R. Klein, B. E. Klein (cited above). This too gives a single value for the whole of zone B.

$AVR_B$: This ratio is given by $CRVE_B/CRAE_B$.

1.4.3 Zone C Vessel Measurements

Let v be a vessel. The following vessel Zone C measurements include all descendent segments of the root segment within the Zone that are combined in a novel way.

Mean Width $\omega_C(v)$: The mean width of a vessel v, in Zone C, is a recursive combination of the root segment and its descendants, where $$\hat{w}(s) = \frac{w_C(s)\lambda_C(s) + a_v \sqrt{\left(\hat{w}(s_1)^2 + \hat{w}(s_2)^2\right)} \frac{\lambda_C(s_1) + \lambda_C(s_2)}{2}}{\lambda_C(s) + \frac{\lambda_C(s_1) + \lambda_C(s_2)}{2}}$$

Where s1 and s2 are the daughter segments of s; and $$a_v = \begin{cases} 0.88 & \text{if } v \text{ is an arteriole} \\ 0.95 & \text{if } v \text{ is a venule} \end{cases}$$

Standard Deviation $\omega_C(v)$: The standard deviation of a vessel v in Zone c is given as follows:

$$sd_C(v) = \frac{\sum_{s \in v} \sigma_C(s)\lambda_C(s)}{\sum_{s \in v} \lambda_C(s)}$$

$CRVE_C$: The widths of the six largest venules in Zone C are combined using the formula given in M. D. Knudtson, K. E. Lee, L. D. Hubbard, T. Y. Wong, R. Klein, B. E. Klein (cited above). This gives a single value for the whole of zone C.

$CRAE_C$: The widths of the six largest arterioles in Zone C are combined using the formula given in M. D. Knudtson, K. E. Lee, L. D. Hubbard, T. Y. Wong, R. Klein, B. E. Klein (cited above). This too gives a single value for the whole of zone C.

$AVR_C$: This ratio is given by $CRVE_C/CRAE_C$.

Simple Tortuousity st(v): The measure is the weighted average of the simple tortuotisty of the vessel segments of v in Zone C as given by:

$$st(v) = \frac{\sum_{s \in v}^{T_C}(s)\lambda_C(s)}{\sum_{s \in v}\lambda_C(s)}$$

Curvature Tortuousity ct(v): The measure is the weighted average of the curvature tortuotisty of the vessel segments of v in Zone C as given by:

$$ct(v) = \frac{\sum_{s \in v}\varsigma_C(s)\lambda_C(s)}{\sum_{s \in v}\lambda_C(s)}$$

1.4.4 Branching Measurements

The following measurements describe the branching properties of the root segment and its daughter segments.

Branching Coefficient, bc(v) where bc(v) is defined on vessels. bc(v)=beta(root(v)) where root(v) refers to the root segment of v.: Beta(s) is a function of s, where s is an element from the set of all segments. Beta of a segment s is defined as $$\beta(s) = \frac{\omega(s_1)^2 + \omega(s_2)^2}{\omega(s)^2}$$

where $s_1$ and $s_2$ are daughters of s and â was adapted from the area ratio described in M. Zamir, J. A. Medeiros, T. K. Cunningham. Arterial Bifurcations in the Human Retina, Journal of General Physiology, 1979 Oct, 74(4): 537-48.

Asymmetry Ratio ar(v): The asymmetry ratio, presented in M. Zamir, J. A. Medeiros, T. K. Cunningham (cited above), is given as ar(v)=α(root(v)) where root(v) refers to the root segment of vessel, v.

$$\alpha(s) = \left(\frac{\min(\omega(s_1), \omega(s_2))}{\max(\omega(s_1), \omega(s_2))}\right)^2$$

where $s_1$ and $s_2$ are daughters of s.

Junctional Exponent Deviation, je(v): The junctional exponent is given in R. Maini, T. MacGillivary, T. Aslam, I. Deary, B. Dhillon. Effect of Axial Length on Retinal Vascular Network Geometry, American Journal of Opthalmology, Volume 140, Issue 4, Pages 648.e1-648.e7, and has a theoretical value of 3. The junctional exponent deviation expresses the deviation from the value of 3 as a percentage of the root segment where:

$$\rho(s) = \frac{\sqrt[3]{|\omega(s)^3 - \omega(s_1)^3 - \omega(s_2)^3|}}{\omega(s)},$$

$s_1$ and $s_2$ are daughters of s and je(v)=ρ(root(v)).

Branching Angle (as described in M. Zamir, J. A. Medeiros, T. K. Cunninghan, cited above), ba(v): The branching angle of the vessel is computed by measuring the angles between the centreline of the segments, s, and its daughter segments s1, s2 near the branching point. For each segment, s, s1, s2, 9 pairs of points are used to measure the gradient and the average gradient is used to calculate the daughter angles whose sum give the branching angle.

Angular Assymmetry, aa(v): This measures the absolute difference in the daughter angles.

1.4.5 Other Measurements

Other measurements may be obtained that do not relate directly to Zones B and C or vessels. One possibility is the length Diameter Ratio (described in N. Witt, T. Y. Wong, A. D. Hughes, N. Chaturvedi, B. E. Klein, R. Evans, Ma. McNamara, S. A. McG Thom, R Klein. Abnormalities of Retinal Microvascular Structure and Risk of Mortality From Ischemic Heart Disease and Stroke, Hypertension, 2006, 47:975-981), ldr(v): A segment s is qualified to participate in the ratio if and only if it is a segment that occurs after the first branching point of the vessel v but before the second branching point and the entire qualified segment is within Zone C. The length diameter ratio of vessel v is that defined as the ratio of the length of the qualified segment to the average diameter of the segment.

1.5 Further Editing

Figure 9:
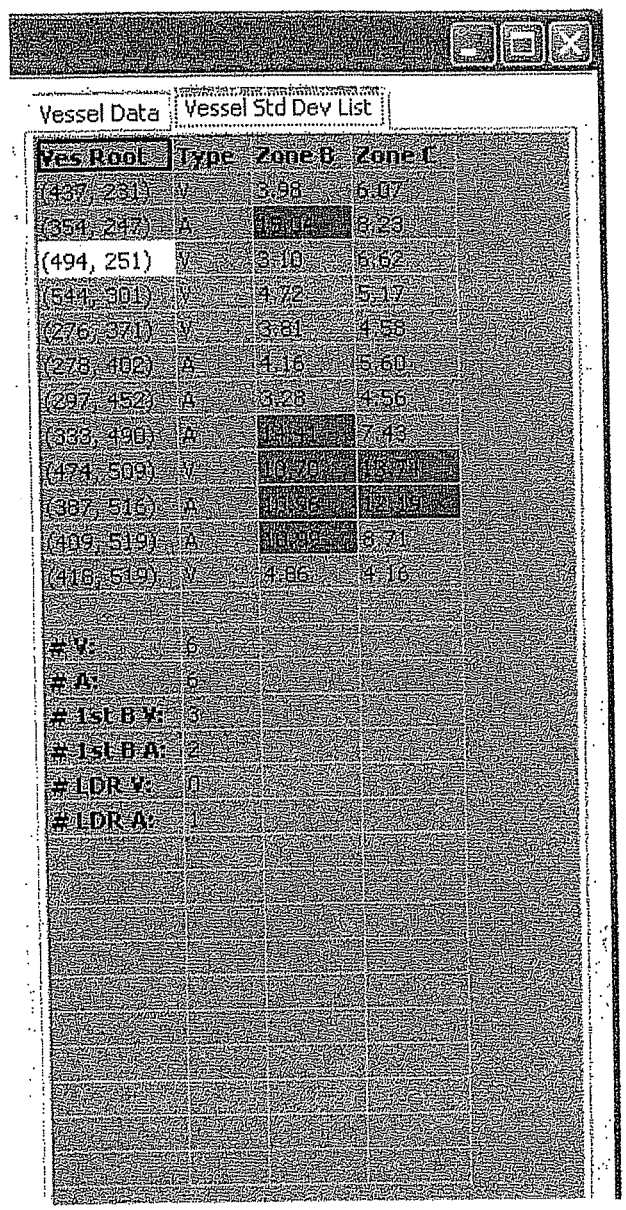
FIG. 9 is a screenshot showing the list of vessels and their standard deviation of vessel widths in the respective zones, generated by the method of FIG. 2.

The set of data generated by the attribute constructor 14e in relation to a vessel is displayed (step 9) as illustrated in FIGS. 8 and 9. FIG. 9 highlights vessels with wide variations in width measurements for the user to edit. The dataset is shown as 17 in FIG. 3. It includes the segment measurement data produced in step 1.4.1.

Figure 5:
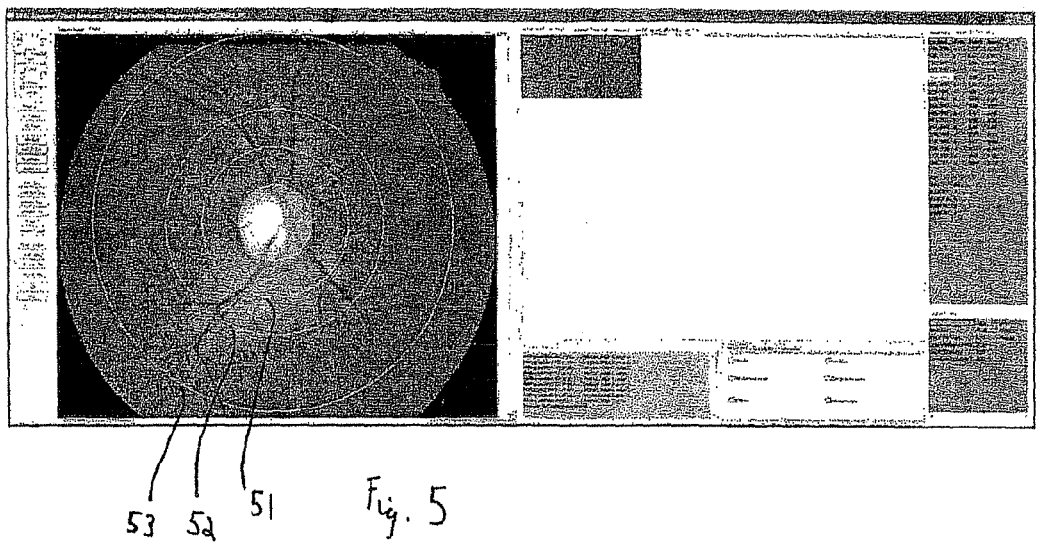
FIG. 5 is a screenshot of a digital retinal image produced by the embodiment of FIG. 2, showing the assigned optic disc.

FIG. 5 shows the overall appearance of the GUI 12 at this time with the outer boundaries of the zones A, B and C indicated by circular lines 51, 52, 53, and the dataset of FIG. 8 inset.

Figure 10:
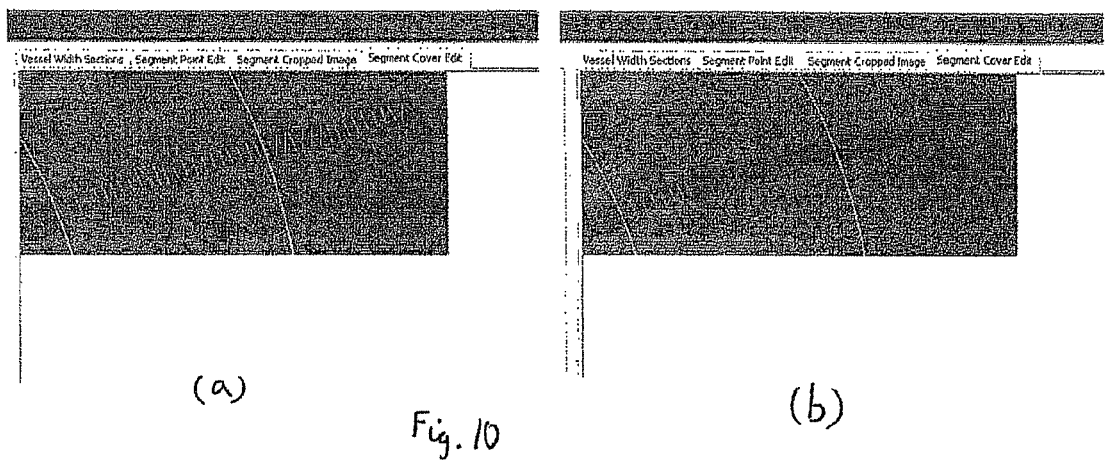
FIG. 10 is composed of FIGS. 10(a) and 10(b), which are screenshots showing the removal of lines from the trace image which cause large variations in the standard deviation of the vessel width in the method of FIG. 2.

There is then a user-interactive process of refinement of the data using the segment editor 12d, thereby editing the segments (step 10), such as editing their widths. FIG. 10 illustrates a manual discarding of bad widths by the user as part of editing the segment in step 10. Widths involved in computing the measures are shown in bright lines along the segment. In FIG. 10a, all widths are used. FIG. 10b shows discarded bad widths as dark lines that were removed by the user. The user may discard or include widths by dragging the mouse across them or clicking on them. For further control, the user may choose to modify each width (bright line in FIG. 10a) by manually shifting them or changing their length. Vessels that fail to fall within an acceptable standard deviation for width are highlighted, so that the user may decide whether to further edit them. The editing process allows a user to remove visual obstructions when inspecting the image and editing the centrelines of the trace paths. The loop through steps 8, 9 and 10 can be performed until the user is satisfied that enough width measurements are taken and the standard deviation is acceptable for each vessel.

1.6 Export of Data (Step 11)

Under the control of a data exporter unit 12e of the GUI, the extractor unit 14f of the attribute extraction module 14 then outputs (e.g. in response to the user inputting an instruction "save") the list of vessels and their standard widths in the respective zones, as illustrated in FIG. 9. The data may be sent to a data store for subsequent analysis.

This aggregated data is labelled 18 in FIG. 3, and is output from the system as "output attributes". It is a table of values in comma separated value (csv) format.

These output attributes may be used to predict medical conditions, for example in the following way:
1. The output is in table format where each image is an instance (row) in the table and the attributes are the columns.
2. Each instance is labelled with the presence or absence of disease.
3. Standard statistical correlation methods or modern classification methods (such as, Support Vector Machines, Bayesian networks) may be used to build predictive models with the labelled data as training data.

2. Second Aspect of the Invention

In the examples described herein, Diabetic Retinopathy Study Field 2 (disc centred) retinal photographs are used to calculate the fractal dimension. Colour retinal photographs were taken after pupil dilation using a Zeiss FF3 fundus camera, which were then digitized. The fractal dimension is sensitive to magnification differences, the angle of view and the retinal photography field and these factors should be borne in mind when comparing fractal dimensions. Embodiments of the present invention can calculate a fractal dimension for other retinal photography fields, such as field 1 and macular centred, but the fractal dimension will be different from other fields taken of the same eye.

A diagnostic retinal image method 200 which is an embodiment of the present invention will now be described with reference to the general flow diagram shown in FIG. 12 and FIGS. 13 to 22.

The method 200 includes at 210 acquiring the retinal image to be analysed, which can include retrieving a retinal image from the data store 150. The size of the retinal image can be adjusted and can be sized to fill one of the displays 130.

Figure 13:
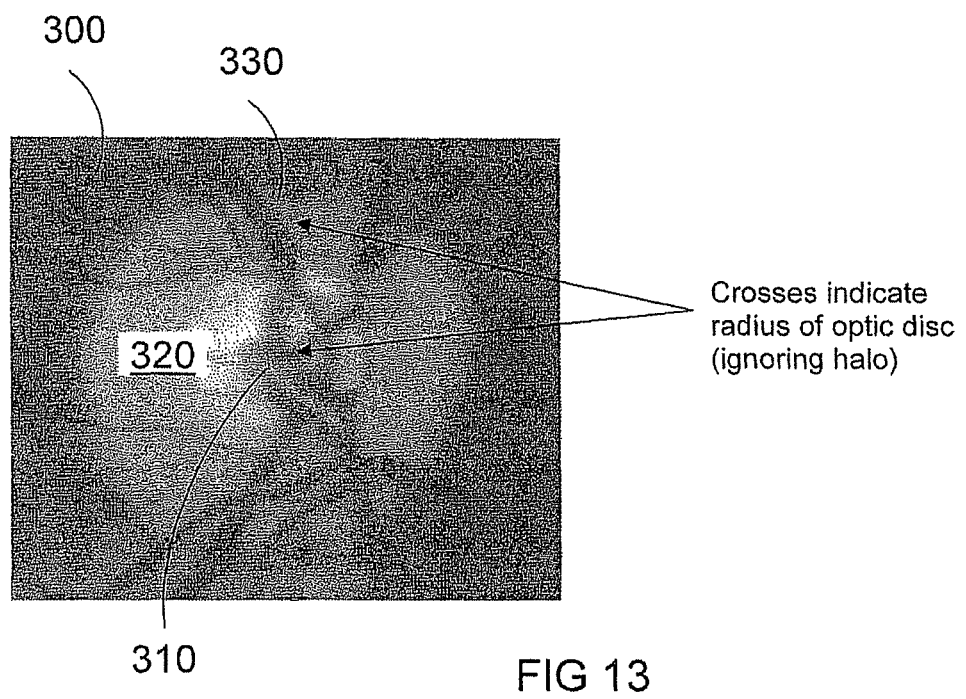
FIG. 13 is a screenshot of a digital retinal image showing setting a radius of the optic disc according to embodiments of the second aspect of the present invention.

The method 200 includes at 220 setting a radius of the optic disc of the retinal image. With reference to the retinal image 300 shown in FIG. 13, the centre 310 of the optic disc 320 is estimated either automatically using a suitable algorithm or manually, which includes a user highlighting the centre 310, for example, with a cross as shown in FIG. 13. An upper edge 330 of the optic disc 320 vertically above the centre 310 is defined either automatically using a suitable algorithm or manually, which includes the user highlighting the upper edge 330, for example, with a cross as shown in FIG. 13. The upper edge 330 is defined to be where the optic disc 320 definitely ends and the colouration becomes that of the background retina or peripapillary atrophy. If there is an optic disc halo, the presence of the halo is ignored, either by the algorithm or the user.

The method 200 includes at 230 cropping or scaling the retinal image 300 to minimise deleterious aspects of the retinal image and enable retinal image comparisons. This includes setting a radius factor, which crops or scales the retinal image 300 to a multiple of the optic disc radius. According to some embodiments, the radius factor can be in the range 2.0-5.0. In preferred embodiments, the radius factor is set to 3.5 such that the size of the retinal image is 3.5 optic disc radii. By cropping the retinal image to a consistent area defined relative to optic disc size, different images from the same individual taken at different times can be compared. Images from different individuals can also be compared because cropping/scaling corrects somewhat for differences in image magnification, refractive error and different angles of photography. A radius factor of 3.5 optic disc radii is used for some of the embodiments because it was found that beyond this radius factor with the equipment used, artefacts, such as shadowing, photograph halos and the like, occur which degrade the image quality.

Figure 12:
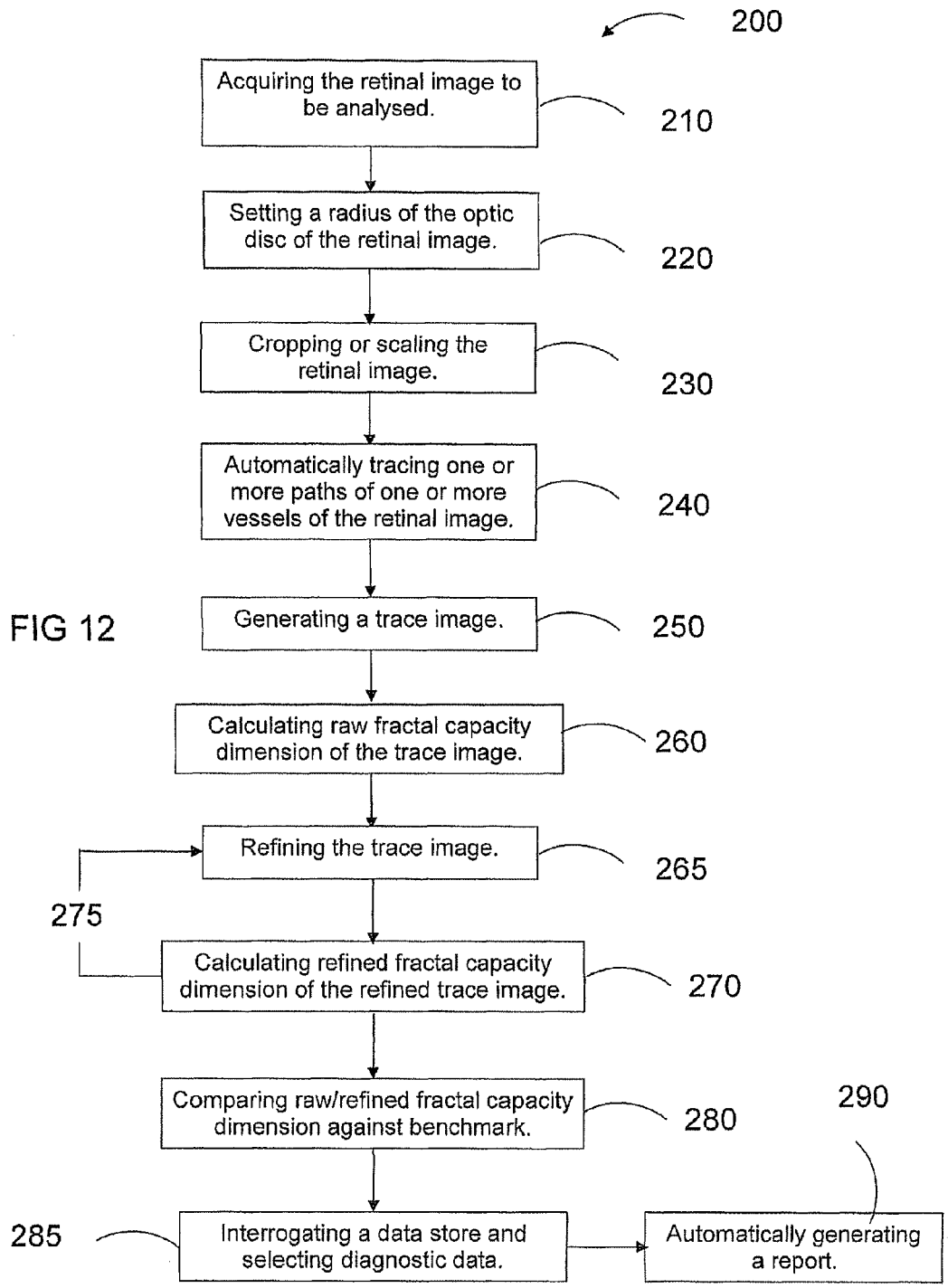
FIG. 12 is a general flow diagram illustrating a method according to embodiments of the second aspect of the present invention.

At 240, the method 200 represented in FIG. 12 includes automatically tracing one or more paths of one or more vessels of the retinal image 300. According to some embodiments, the starting points of the vessels can be detected using a matched Gaussian filter and the detected vessels are traced using a combination of a statistical recursive estimator, such as a Kalman filter, and a Gaussian filter. According to other embodiments, the network of vessels is detected by performing a non-linear projection to normalize the retinal image 300. Subsequently, an optimal threshold process is applied to binarize the image. The detected network is then thinned by applying a distance-based centreline detection algorithm.

Figure 14:
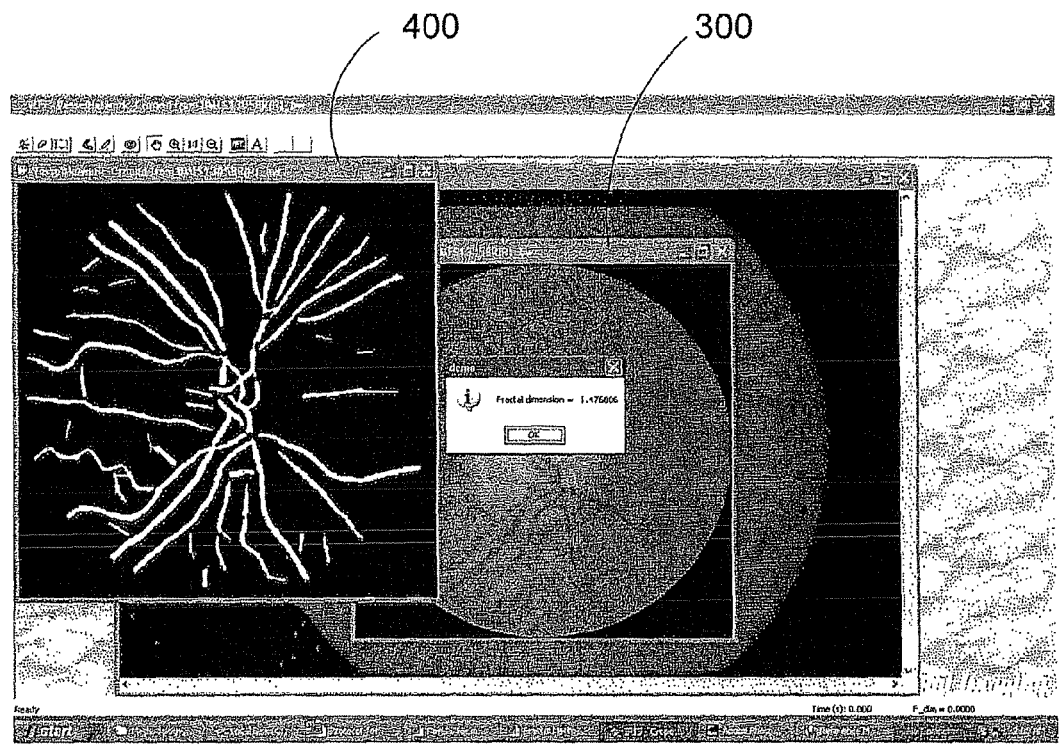
FIG. 14 is a screenshot of a trace image generated from the digital retinal image according to embodiments of the second aspect of the present invention.
Figure 15:
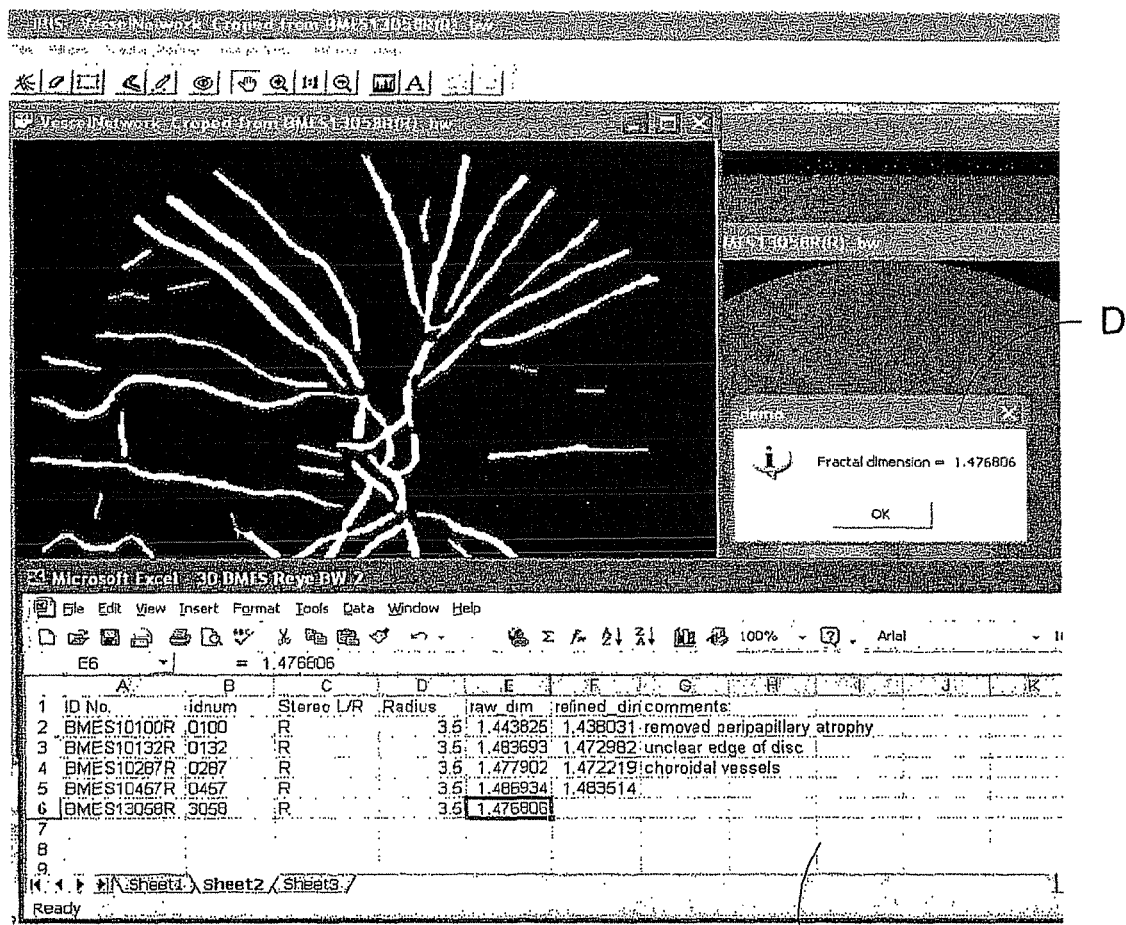
FIG. 15 is a screenshot partially showing an enlargement of the trace image, the digital retinal image and stored data relating to the retinal and trace images according to embodiments of the second aspect the present invention.

The method 200 further includes at 250 automatically generating a trace image 400 comprising the one or more traced paths, an example of which is shown in FIG. 14 partially overlaid on the retinal image 300.

At 260, the method includes automatically calculating a raw fractal capacity dimension of the trace image. According to some embodiments, a box-counting method known from, for example, Stosic, T. & Stosic, B. D., Multifractal analysis of human retinal vessels, IEEE Trans. Med. Imaging 25, 1101-1107 (2006) is employed. For each trace image 400, the method includes automatically selecting 1000 points at random on each trace image structure. Each structure has a typical size $M_0$ of 30,000 pixels and a typical linear size L of 600 pixels. The number of pixels $M_i$ inside boxes centred on each point are then automatically counted. The method includes extracting the generalized dimension $D_q$ from these numbers for different values of q ($-10<q<10$) as slopes of the lines obtained through minimum squares fitting of log $\{[M(R)/M_0]^{q-1}\}/(q-1)$ as a function of log (R/L) where R is the growing linear dimension of the boxes. Preferred embodiments of the method include repeating the process, for example, 100 times, with the random selection of points repeated each time and the final values of $D_q$ calculated from the average of the repetitions. The fractal capacity dimension $D_0$, of course, corresponds to q=0.

In this example, the fractal capacity dimension D is 1.476806, as displayed in FIG. 14. The raw fractal capacity dimension including all the decimal place values is recorded in the data store 150 along with an identifier for the retinal image file, such as a unique filename, an identification number of the patient to whom the retinal image belongs, whether the image is of the left or right eye and the optic disc radius. In the example shown in FIG. 15, this data is recorded in a spreadsheet 500, but any other suitable file, such as a machine-readable .csv file, can be used, from which a report can be complied as described in further detail hereinafter and which can be used for subsequent research. The trace image 400 and/or the retinal image 300 can be resized and displayed side by side, for example, with one image in each display 130, for ease of comparison.

Some the method 200 includes at 265 refining the trace image 400 to remove errors in the trace image. The vessel trace function of the present invention is sensitive and will pick up fine arterioles and venules as well as artefacts that are not vessels, such as peripapillary atrophy, choroidal vessels or light reflected from the nerve fibre layer. The term "error" in relation to the trace image is used herein to refer to artefacts that are not vessels. Refining of the trace image can be executed automatically by a suitable algorithm or manually.

Refining of the trace image 400 will now be described in more detail with reference to FIGS. 16-20.

Figure 16:
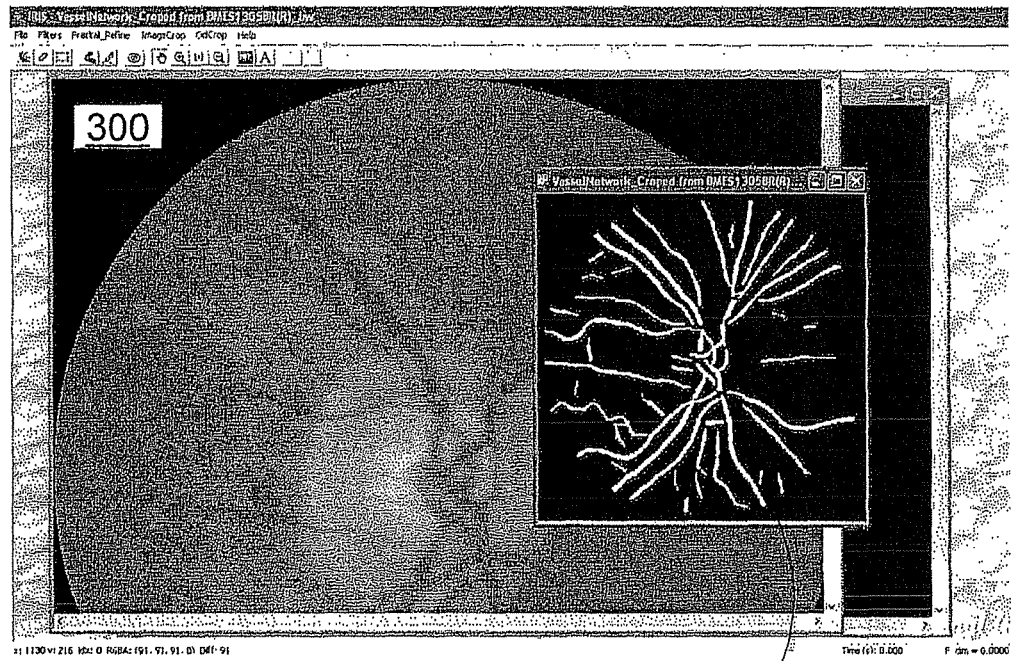
FIG. 16 is a screenshot showing the trace image and an enlarged digital retinal image during refining of the trace image according to embodiments of the second aspect of the present invention.
Figure 17:
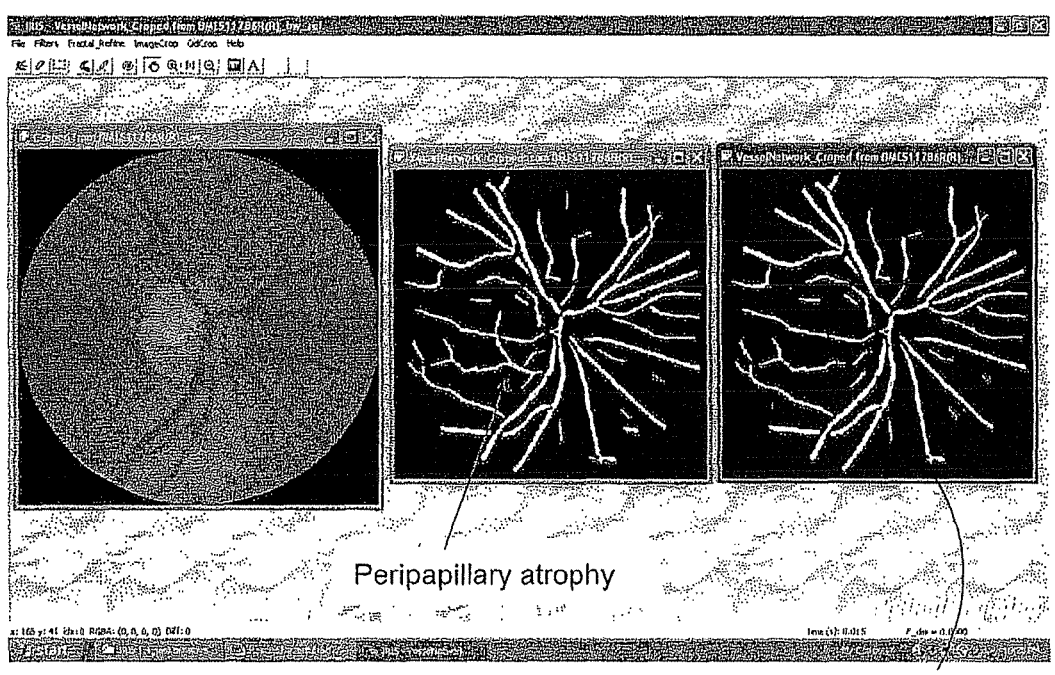
FIG. 17 is a series of screenshots showing the removal of peripapillary atrophy from the trace image during refining of the trace image according to embodiments of the second aspect of the present invention.

Refining includes comparing each line tracing in the trace image 400 with the corresponding area in the retinal image 300. Manually, the user can start, for example, at the 12 o'clock position on the trace image 400 and move clockwise around the image. The feature that each tracing is derived from should be identified as a vessel or otherwise. Where it is difficult to determine if a line trace is a vessel or an artefact, the retinal image 300 and/or the trace image 400 can be enlarged as required for improved comparison. An example is shown in FIG. 16, where vessel tracings at the 10 o'clock position require closer examination to determine if they are artefacts or true vessels. In FIG. 6, the vessel tracings at the 10 o'clock position are true retinal vessels.

If a line tracing in the trace image 400 cannot be linked to a retinal vessel in the retinal image 300, the incorrect line tracing or error can be erased from the trace image 400. This can be executed automatically or manually. Where executed manually, an erase function known from electronic drawing packages can be employed to erase the erroneous line tracing. Any small white pixels left behind in the trace image 400 must also be erased and it may be necessary to enlarge the trace image 400 to ensure all of the tracing has been removed.

When refining the trace image 400, a range of artefacts can occur and must be removed from the trace image to ensure they do not affect the fractal dimension calculation. For example, abnormalities around the optic disc 320, such as peripapillary atrophy, must be removed, as shown in the series of images in FIG. 7, to produce a refined trace image 700. Other artefacts that must also be removed include unusual line tracings that do not correspond to vessels, especially short, thick lines, any clear artefacts, such as horizontal lines at the top or bottom of the image and any isolated short lines at an unusual angle and which do not come off any major vessels. Any pigment abnormalities can be erroneously traced as vessels, particularly with poorly focused retinal images. Such tracings, as well as retinal haemorrhages, should also be removed from the trace image 400.

The series of images in FIG. 18 shows the removal of short lines which do not correspond to vessels to produce a refined trace image 800. Note their short length, unusual orientation, and lack of connection to existing vessels. The series of images in FIG. 19 shows the removal of choroidal vessels at the 6 o'clock position to produce a refined trace image 900. The series of images in FIG. 20 shows the removal of artefacts at the 5 o'clock position to produce a refined trace image 1000.

Once all incorrect tracings or errors in the trace image 400 have been erased embodiments of the method 200 include at 270 calculating a refined fractal capacity dimension of the refined trace image. The refined fractal dimension $D_0$ will be equal to or less than the raw fractal dimension. In the aforementioned example, the refined fractal dimension is 1.472857 compared with the raw fractal dimension of 1.476806. The refined fractal dimension and any comments are also recorded in the data store 150.

The method 200 includes at 275 repeating refining of the trace image 400 if errors in the trace image remain after previous refining, i.e. any incorrect tracings remaining in the refined fractal trace image can be erased and a further refined trace image generated along with another refined fractal dimension. Both the further refined trace image and the further refined fractal dimension are also saved in the data store 150, for example, in the same text file, with the previous data.

According to some embodiments, the cropped/scaled image file and the refined fractal trace image file can be saved. In some embodiments, the raw fractal line tracing can be discarded because it can be generated from the cropped/scaled image file. This will allow rechecking of results later if required.

Figure 21:
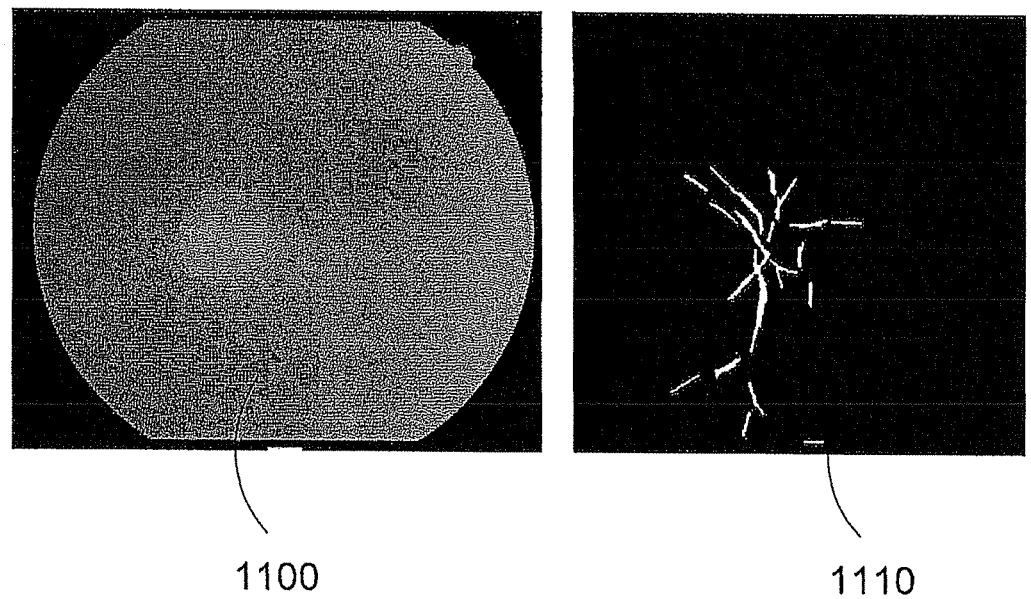
FIG. 21 is a pair of screenshots showing a retinal image and an ungradable trace image according to embodiments of the second aspect of the present invention.

An image is defined as ungradable if the program cannot trace one or more of the major vessels. FIG. 21 shows an example of an ungradable retinal image 1100 and the initial trace image 1110. That a retinal image is ungradable is recorded in the data store 150.

At 280, the method 200 includes comparing the calculated fractal capacity dimension with a benchmark fractal capacity dimension. The benchmark fractal capacity dimension is determined from a large number of measurements of the fractal capacity dimension from a 'normal' population without hypertension or diabetes etc.

At 285, the method 200 includes generating a diagnosis by interrogating a data store and selecting diagnostic data based on, or correlating to, the comparison of the calculated raw or refined fractal capacity dimension with the benchmark fractal capacity dimension. The calculated fractal capacity dimension provides an accurate description of the retinal vasculature and subtle changes in the retinal vasculature are reflected in changes in the fractal capacity dimension. Such changes can be linked to, and be indicators of, cardiovascular disease and other conditions, such as hypertension and diabetes.

Figure 22:
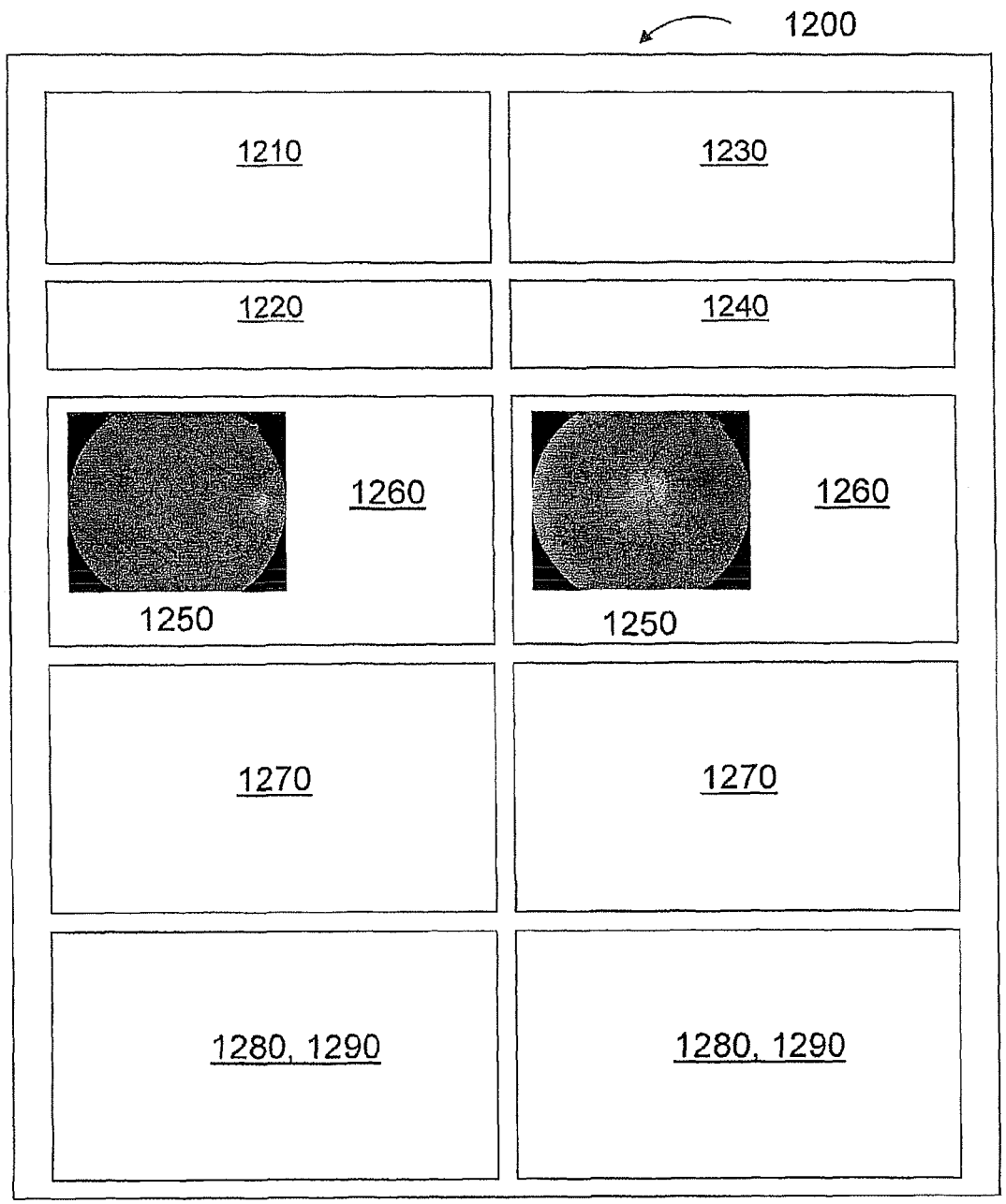
FIG. 22 shows an example of a report produced in accordance with embodiments of the second aspect of the present invention.

With reference to FIG. 12, at 290, embodiments of the method 200 include the processor 110 automatically generating a report including the retrieved diagnostic data 1280, which is discussed in further detail herein. A schematic example of a report 1200 is shown in FIG. 22. According to some embodiments, the report 1200 comprises patient data 1210, such as name, age, date of birth, gender, address, ID number, and the like. The patient data can be entered by the user, or the data fields can be automatically populated by the processor 110, for example, by retrieving information from the data store 150 or a dedicated patient database (not shown) coupled to be in communication with the processor 110. The report 1200 also comprises medical information 1220 about the patient, such as their blood pressure, whether they are a diabetic, their smoking status and history and the like. Requesting practitioner details 1230 can also be included, the date the retinal images were taken and the date of the report 1240. One or more retinal images 1250 of the patient, one or more trace images and/or one or more refined trace images can be included. Associated measurements 1260 determined from the fractal analysis can also be included.

The particular diagnostic data 1280 retrieved from the data store 150 and included in the report 1200 is based on, or correlates to, the comparison of the calculated fractal capacity dimension with the benchmark fractal capacity dimension. For example, diagnostic data 1280 in the form of clauses or statements based on the calculated refined fractal capacity dimension are retrieved from the data store 150 and inserted in the report 1200. The particular diagnostic data retrieved can also depend on one or more other characteristics of the patient, such as, but not limited to, their age, blood pressure, whether they are or have been a smoker, whether they are a diabetic and/or their family medical history. For example, a calculated refined fractal capacity dimension within a specific range and/or above or below a specific threshold, possibly combined with the one or more items of the aforementioned patient data 1210, cause specific diagnostic data 1280 to be retrieved from the data store 150 and inserted in the report 1200. An estimate for future risk of cardiovascular disease and other diseases on the basis of the comparison is thus provided. Examples of specific diagnostic data 1280 include, but are not limited to "Increased risk of hypertension and coronary heart disease", "Progression of diabetic retinopathy, kidney diseases and increased deaths from stroke", "High risks of stroke, coronary heart disease and cardiovascular mortality" and "High risk of glaucoma". References to medical reports and papers supporting the diagnosis can also be included.

Other pathology 1290 can also be included in the report 1200. In some embodiments, this can be produced from diagnostic data retrieved from the data store 150 and from the data recorded for the patient. The diagnostic data 1280 and other pathology 1290 can be stored, for example, in a look-up table or via any other suitable means known in the art.

The fractal capacity dimension can be a mono-fractal capacity dimension, but in preferred embodiments, the fractal capacity dimension is a multifractal capacity dimension because this more appropriately describes fractal characteristics of the retinal vasculature. A multifractal can be considered as multiple monofractals embedded into each other, the multifractal having a hierarchy of exponents rather than a single fractal dimension.

Results obtained with embodiments of the present invention were based on a random sample of 60 black and white optic disc centred retinal photographs of right eyes from a study comprising 30 participants without hypertension and diabetes, 15 participants with hypertension only and 15 participants with diabetes only. At the same visit that retinal photography was performed, the systolic blood pressure (SBP) and diastolic blood pressure (DBP) of each participant was measured using the same mercury sphygmomanometer with appropriate adult cuff size, after seating the participant for at least 10 minutes. The 2003 World Health Organization (WHO)/International Society of Hypertension (ISH) guidelines were adapted to define hypertension. The subject was considered hypertensive grade 2 or above (severe hypertension) if the subject was previously diagnosed as hypertensive and currently using anti-hypertensive medications, or had a SBP≥160 mmHg or a DBP≥100 mmHg at examination. Diabetes was defined based on a physician diagnosis of diabetes, or a fasting blood sugar ≥7 mmol/L.

Table 1 below shows the baseline characteristics of the sample population (n=60). The age range was 50-86 years and 52% of the sample was male.

TABLE 1

|  | Mean (range or %) |
| --- | --- |
| Age (yrs) | 62.4 (50-86) |
| Systolic blood pressure (mmHg) | 135 (110-200) |
| Diastolic blood pressure (mmHg) | 79 (53-118) |
| Male | 31 (52) |
| Hypertensive | 15 (25) |
| Diabetic | 15 (25) |

Figure 23:
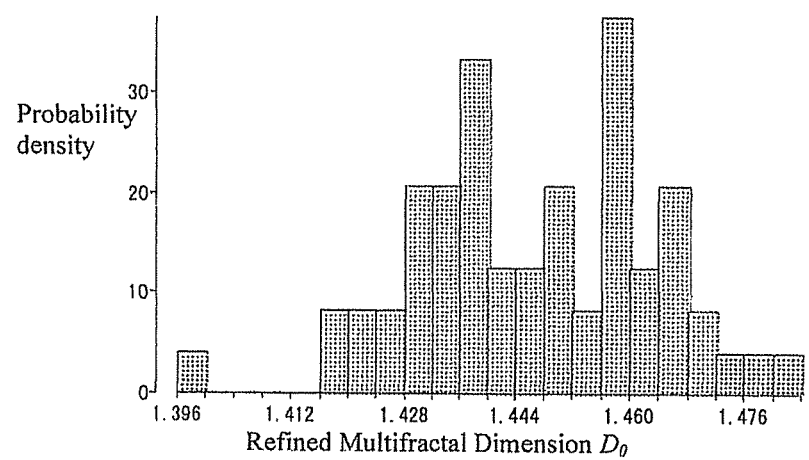
FIG. 23 shows a distribution of refined multifractal dimension $D_0$.

With reference to FIG. 23, the value of the refined multi-fractal dimension $D_o$ is approximately normally distributed. The mean multi-fractal dimension in this study sample is 1.447 with a standard deviation of 0.017. This is lower than the often quoted fractal dimension of 1.7 because embodiments of the present invention calculate the multifractal capacity dimension, which is lower than the diffusion limited aggregation (monofractal) dimension of 1.7.

Reliability estimates of embodiments of the present invention have been determined from the aforementioned study sample. Colour photographs of the same right eye retinal field of the 30 participants without hypertension and diabetes were also graded and the results compared with the identical, but black and white, photographs. Comparison was made between three graders and agreement assessed used Pearson correlation coefficients. Table 2 below shows that the intra- and inter-grader reliability estimates were generally high, with correlation of over 0.90. Reliability estimates were higher for refined fractal dimension $D_0$ compared to the raw fractal dimension.

TABLE 2

|  | Correlation coefficient | |
| --- | --- | --- |
|  | Raw multifractal dimension | Refined multifractal dimension ($D_0$) |
| Intra-grader | | |
| Grader 1 (1 week apart) | 0.93 | 0.93 |
| Grader 2 (1 week apart) | 0.95 | 0.93 |
| Grader 3 (1 week apart) | 0.95 | 0.95 |
| Inter-grader | | |
| Grader 1 vs grader 2 | 0.92 | 0.91 |
| Grader 1 vs grader 3 | 0.92 | 0.90 |
| Grader 2 vs grader 3 | 0.94 | 0.93 |
| TIFF photos vs JPEG photos | 0.97 | 0.97 |
| Colour photos vs black & white | 0.70 | 0.79 |

It will be noted that embodiments of the present invention can be applied to both colour images and black and white images. There is a small discrepancy between the calculated fractal dimension, but the correlation between the raw fractal dimension calculated from colour and black and white photographs is moderately high (0.70-0.79). TIFF and JPEG format photos had very high correlation of 0.97. Embodiments of the present invention exhibit robustness to use by different users (graders). Even with the raw multi-fractal dimension, i.e. after setting the optic disc radius, but before removing artefacts, the intra-grader reliability is high (correlation 0.93), while the refined dimension, i.e. after refining the trace image 400 to remove artefacts, shows the same correlation.

The correlation of the raw and refined multifractal capacity dimension $D_0$ with a range of systemic and ocular factors were examined, including age, SBP, DBP, refractive error and arteriolar and venular calibre. The refractive error is calculated as the spherical equivalent refractive error (SER)= spherical power+½ cylindrical power). The arteriolar and venular calibre is represented by the central retinal arteriole and venule equivalents (CRAE and CRVE respectively). The arteriolar and venular calibres were calculated using a computer-assisted method as described in Liew, G. et al. Measurement of retinal vascular calibre: issues and alternatives to using the arteriole to venule ratio. Invest Opthalmol Vis. Sci. 48, 52-57 (2007). The results are shown in Table 3 below and the numbers in the table refer to the Pearson correlation coefficients.

TABLE 3

|  | Correlation coefficients | | | |
| --- | --- | --- | --- | --- |
|  | Raw multifractal dimension | Refined multifractal dimension ($D_0$) | Mean arteriolar calibre (μm) | Mean venular calibre (μm) |
| Age (yrs) | −0.39 | −0.41 | −0.50 | −0.19 |
| Systolic blood pressure (mmHg) | −0.52 | −0.53 | −0.36 | −0.02 |

TABLE 3-continued

| | Correlation coefficients | | | |
|---|---|---|---|---|
| | Raw multifractal dimension | Refined multifractal dimension ($D_0$) | Mean arteriolar calibre (μm) | Mean venular calibre (μm) |
| Diastolic blood pressure (mmHg) | −0.32 | −0.29 | −0.27 | −0.02 |
| Mean arteriolar calibre (μm) | 0.37 | 0.40 | 1.0 | 0.47 |
| Mean venular calibre (μm) | 0.21 | 0.24 | 0.47 | 1.0 |
| Right eye SER | 0.08 | 0.04 | — | — |

Both the refined and raw $D_0$ showed moderate correlation with age, SBP and DBP. Of note, the refined $D_0$ was more highly correlated with both SBP and DBP than arteriolar calibre. Refractive error had very low correlation with raw and refined $D_0$.

With reference to Table 4 below, the refined $D_0$ were compared in participants with and without hypertension. Mean refined $D_0$ was 0.020 (95% confidence interval 0.013 to 0.028) lower in participants with hypertension compared to those without and this difference was highly significant ($p<0.0001$). In Table 4, CI refers to confidence intervals and * denotes using the t-test.

TABLE 4

| Hypertension | No. of Eyes | Mean refined multifractal dimension, $D_0$ (95% CI) | Difference (95% CI) | P value* |
|---|---|---|---|---|
| Absent | 45 | 1.453 (1.449-1.458) | — | — |
| Present | 15 | 1.433 (1.427-1.440) | 0.020 (0.013 to 0.028) | <0.0001 |

Figure 24:
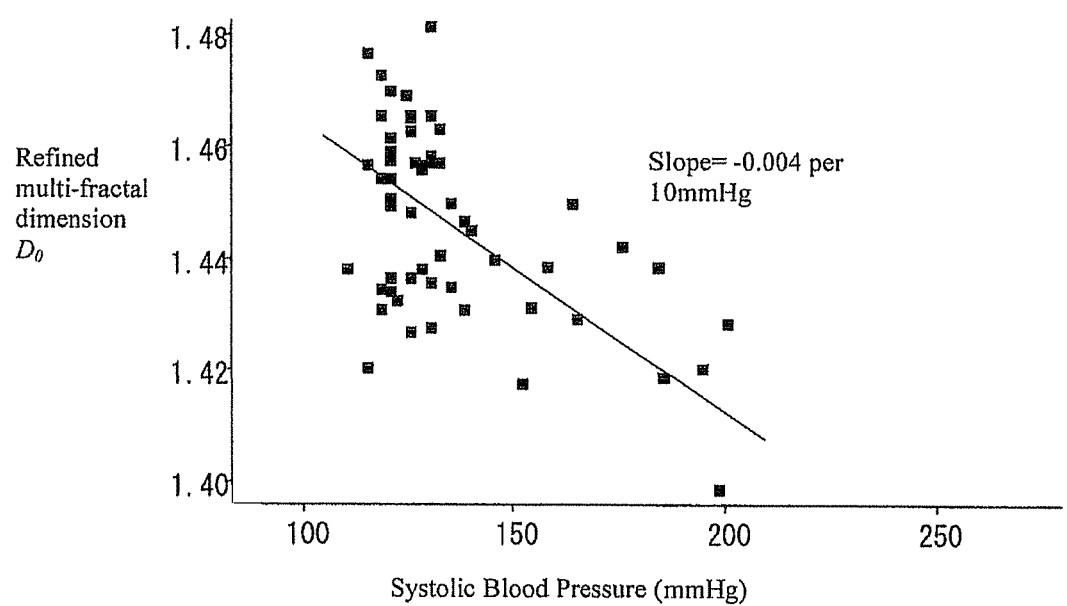
FIG. 24 shows a graph of refined multifractal capacity dimension in a whole sample of participants plotted against systolic blood pressure.

FIG. 24 shows a graph of refined $D_0$ in the whole sample plotted against SBP. The inverse relationship of the refined $D_0$ with SBP shows $D_0$ decreasing by 0.004 per 10 mmHg increase in SBP.

The multi-fractal dimension shows strong correlation with SBP, DBP and age, as well as with CRAE and CRVE. Indeed, the correlation of multi-fractal dimension with SBP and DBP is even higher than that of CRAE with SBP and DBP suggesting that calculating the multi-fractal capacity dimension is better than CRAE for detecting early changes in CVD. Embodiments of the present invention can also detect differences in the multifractal dimension in persons with and without hypertension even in this small sample.

It is envisaged that the arterioles and venules of the detailed digital retinal images 300 could be isolated and the raw and refined fractal capacity dimensions calculated for arterioles only and venules only thus potentially providing an even stronger correlation between the fractal capacity dimension and vascular diseases, such as, but not limited to, diabetes and hypertension.

With reference to FIG. 1, when the system is configured to perform the second aspect of the invention it further comprises computer readable program code components configured for calculating a refined fractal capacity dimension of the refined trace image. The system also comprises computer readable program code components configured for comparing the calculated fractal capacity dimension with a benchmark fractal capacity dimension and computer readable program code components configured for generating an estimate for future risk of cardiovascular disease on the basis of the comparison. Hence, the diagnostic retinal image system and method of the second aspect of present invention accurately measures the fractal dimension capacity of retinal images automatically to provide an estimate for future risk of vascular diseases, such as, but not limited to, diabetes and hypertension. The superior accuracy of fractals in describing the anatomy of the eye enables accurate measurements of the fractal dimension capacity to reveal subtle changes in the retinal vasculature and thus provide indications of vascular diseases. Embodiments of the second aspect of the invention show strong correlations even with the raw fractal dimension capacity demonstrating that the method and system are robust to grader error.

DEFINITIONS

Throughout the specification the aim has been to describe the invention without limiting the invention to any one embodiment or specific collection of features. Persons skilled in the relevant art may realize variations from the specific embodiments that will nonetheless fall within the scope of the invention.

In this specification, the terms "comprises", "comprising", "including" or similar terms are intended to mean a non-exclusive inclusion, such that a method, system or apparatus that comprises a list of elements does not include those elements solely, but may well include other elements not listed. The term "automatic" is used here to mean that an operation is performed without human interaction (although a human may initiate the operation), whereas the term "semi-automatic" is used to describe an operation which involves human interaction with a computer processing system. An "automated" process may comprise one or more automatic operations and/or one or more semi-automatic operations, so the term "automated" is equivalent to the term "computer-implemented".

The invention claimed is:

1. A retinal image analysis method including:
   (i) defining an optic disc for a retinal image;
   (ii) automatically tracing one or more vessels of the retinal image, each vessel comprising a group of vessel segments including a root segment and a plurality of daughter segments connected to the root segment in a vessel binary tree in which at a plurality of branching points one of said vessel segments branches into two said daughter segments;
   (iii) automatically displaying an image comprising the one or more traced vessels;
   (iv) using the vessel segments to calculate automatically a plurality of parameters; and
   (v) outputting the plurality of parameters;
   wherein the plurality of parameters comprise a parameter characterizing the group of vessel segments, the parameter being a fractal capacity dimension of the image.

2. A method according to claim 1 in which the parameters comprise parameters which describe a corresponding one of the vessel segments, and comprise one or more of:
   a mean width of the vessel segment;
   a value indicative of the variation in the width of the vessel segment along at least part of the length of the vessel segment;
   the length of the vessel segment; and
   the tortuosity of the vessel segment.

3. A retinal image analysis method according to claim 1 comprising deriving a plurality of zones of the retinal image, said step (iv) including deriving one or more said parameters for any portions of the vessel segments which lie within each of the zones.

4. A retinal image analysis method according to claim 3 in which the zones encircle an optic disc region of the retinal image, and have different respective diameters.

5. A retinal image analysis method according to claim 3 in which the group of vessel segments extend within one of the zones.

6. A retinal image analysis method according to claim 1 further comprising obtaining a parameter characterizing the group of vessel segments in which the parameters characterizing the group of vessel segments are selected from the list consisting of:
   a branching coefficient;
   an asymmetry ratio;
   a junctional exponent deviation;
   a branching angle indicative of the an average of the angles between the extension direction of the daughter segments and that of the root segment; and
   an angular asymmetry value indicative of the variance in said angles.

7. A retinal image analysis method according to claim 1 further including classifying vessels into veins and arteries.

8. A retinal image analysis method according claim 7 further including obtaining for at least one said zone a said parameter indicative of the width of a number of the widest veins or of the width of a number of the widest arteries in the zone.

9. A retinal image analysis method according to claim 1 including:
   an editing step of interacting with a user to edit the image displayed in step (iii), the group of vessel segments, or both the image displayed in step (iii) and the group of vessel segments; and
   wherein steps (iv) and (v) are performed, repeated, or both performed and repeated after said editing step.

10. A retinal image analysis method according to claim 1 including indicating any of said vessel segments which are determined in step (iv) to have a variance in their width above a threshold.

11. A retinal image analysis method according to claim 1 including a step of obtaining user annotation of features of the retinal image.

12. A retinal image analysis method according to claim 1 further including generating an estimate for future risk of cardiovascular disease using the plurality of parameters.

13. A retinal image analysis method according to claim 1 in which the fractal capacity dimension is:
   automatically calculated;
   compared with a benchmark fractal capacity dimension; and
   used to generate an estimate for future risk of vascular disease on the basis of the comparison.

14. A retinal image analysis system comprising:
   a processor for:
   (i) defining an optic disc for the retinal image;
   (ii) automatically tracing one or more vessels of the retinal image, each vessel comprising a group of vessel segments including a root segment and a plurality of daughter segments connected to the root segment in a vessel binary tree in which at a plurality of branching points one of said vessel segments branches into two said daughter segments;
   (iii) automatically displaying an image comprising the one or more traced vessels;
   (iv) using the vessel segments to calculate automatically a plurality of parameters; and
   (v) outputting the plurality of parameters;
   wherein the plurality of parameters comprise a parameter characterizing the group of vessel segments, the parameter being a fractal capacity dimension of the trace image.

15. A retinal image analysis system comprising a plurality of computer readable program code components embodied on a non-transitory computer readable medium, the plurality of computer readable program code components comprising:
   (i) computer readable program code components configured for defining an optic disc for a retinal image;
   (ii) computer readable program code components configured for automatically tracing one or more vessels of the retinal image, each vessel comprising a group of vessel segments including a root segment and a plurality of daughter segments connected to the root segment in a vessel binary tree in which at a plurality of branching points one of said vessel segments branches into two said daughter segments;
   (iii) computer readable program code components configured for automatically displaying an image comprising the one or more traced vessels;
   (iv) computer readable program code components configured for using the vessel segments to calculate automatically a plurality of parameters; and
   (v) computer readable program code components configured for outputting the plurality of parameters;
   wherein the plurality of parameters comprise a parameter characterizing the group of vessel segments, the parameter being fractal capacity dimension of the image.

16. A retinal image analysis method including:
   (i) defining an optic disc for a retinal image;
   (ii) automatically tracing one or more vessels of the retinal image, each vessel comprising a group of vessel segments including a root segment and is plurality of daughter segments connected to the root segment in a vessel binary tree in which at as plurality of branching points one of said vessel segments branches into two said daughter segments;
   (iii) automatically displaying an image comprising the one or more traced vessels;
   (iv) using the vessel segments to calculate automatically a plurality of parameters; and
   (v) outputting the plurality of parameters;
   wherein the method further includes classifying the traced vessels into veins and arteries based on intensity profiles of diameter lines along each of the traced vessels, wherein the intensity profiles of the diameter lines comprise histograms of pixel intensities for pixels lying on the respective diameter lines, and wherein the plurality of parameters comprise parameters associated with the veins, parameters associated with the arteries, or both parameters associated with the veins and parameters associated with the arteries.

17. A method according to claim 16 in which a mean value is obtained for each of the intensity profiles of the diameter lines, wherein the mean values are clustered into one of two classes corresponding to veins and arteries.

18. A method according to claim 17 further including using a majority voting system to classify said traced vessels as either veins or arteries based on the number of the diameter lines of Which the corresponding mean values are labeled as veins and arteries respectively.

19. A method according to claim 18, wherein the intensity profiles of diameter lines comprise histograms of pixel intensities for pixels lying on diameter lines.

20. A method according to claim 17, wherein the intensity profiles of diameter lines comprise histograms of pixel intensities for pixels lying on diameter lines.

21. A method according to claim 16, wherein the intensity profiles of diameter lines comprise histograms of pixel intensities for pixels lying on diameter lines.

22. A method according to claim 16, wherein the plurality of parameters comprise a parameter characterizing the group of vessel segments, the parameter being a fractal capacity dimension of the image.

23. A retinal image analysis system comprising:
a processor for:
(i) defining an optic disc for a retinal image;
(ii) automatically tracing one or more vessels of the retinal image, each vessel comprising a group of vessel segments including a root segment and a plurality of daughter segments connected to the root segment in a vessel binary tree in which at a plurality of branching points one of said vessel segments branches into two said daughter segments;
(iii) automatically displaying an image comprising the one or more traced vessels;
(iv) using the vessel segments to calculate automatically a plurality of parameters; and
(v) outputting the plurality of parameters;
wherein the processor is further configured for classifying the traced vessels into veins and arteries based on intensity profiles of diameter lines along each of the traced vessels, wherein the intensity profiles of the diameter lines comprise histograms of pixel intensities for pixels lying on the respective diameter lines, and wherein the plurality of parameters comprise parameters associated with the veins, parameters associated with the arteries, or both parameters associated with the veins and parameters associated with the arteries.

* * * * *